United States Patent
Huang

(10) Patent No.: US 8,568,318 B2
(45) Date of Patent: Oct. 29, 2013

(54) HIGH-RESOLUTION WAVE-THEORY-BASED ULTRASOUND REFLECTION IMAGING USING THE SPLIT-STEP FOURIER AND GLOBALLY OPTIMIZED FOURIER FINITE-DIFFERENCE METHODS

(75) Inventor: Lianjie Huang, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 1548 days.

(21) Appl. No.: 12/033,841

(22) Filed: Feb. 19, 2008

(65) Prior Publication Data

US 2013/0251222 A1  Sep. 26, 2013

Related U.S. Application Data

(60) Provisional application No. 60/901,903, filed on Feb. 16, 2007.

(51) Int. Cl.
*A61B 8/00* (2006.01)

(52) U.S. Cl.
USPC .............................. 600/437; 600/443; 73/584

(58) Field of Classification Search
USPC .................................................. 600/437, 443
See application file for complete search history.

(56) References Cited

U.S. PATENT DOCUMENTS

2006/0287596 A1* 12/2006 Johnson et al. ................ 600/437

OTHER PUBLICATIONS

Thomas, C. "Development of an Inverse Technique to Estimate the Ultrasound Field During Chest Wall and Breast Hyperthermia". U.S. Army Medical Research and Materiel Command. Reported 1996, Public Release 2000 http://www.dtic.mil/docs/citations/ADB225305.*

Huang et al. "Ultrasound pulse-echo imaging using the split-step Fourier propagator". Proc. SPIE 6513, Medical Imaging 2007: Ultrasonic Imaging and Signal Processing, 651305 (Mar. 12, 2007); doi:10.1117/12.709998.*

* cited by examiner

*Primary Examiner* — Unsu Jung
*Assistant Examiner* — Phong K Huynh
(74) *Attorney, Agent, or Firm* — John P. O'Banion

(57) ABSTRACT

Methods for enhancing ultrasonic reflection imaging are taught utilizing a split-step Fourier propagator in which the reconstruction is based on recursive inward continuation of ultrasonic wavefields in the frequency-space and frequency-wave number domains. The inward continuation within each extrapolation interval consists of two steps. In the first step, a phase-shift term is applied to the data in the frequency-wave number domain for propagation in a reference medium. The second step consists of applying another phase-shift term to data in the frequency-space domain to approximately compensate for ultrasonic scattering effects of heterogeneities within the tissue being imaged (e.g., breast tissue). Results from various data input to the method indicate significant improvements are provided in both image quality and resolution.

20 Claims, 24 Drawing Sheets

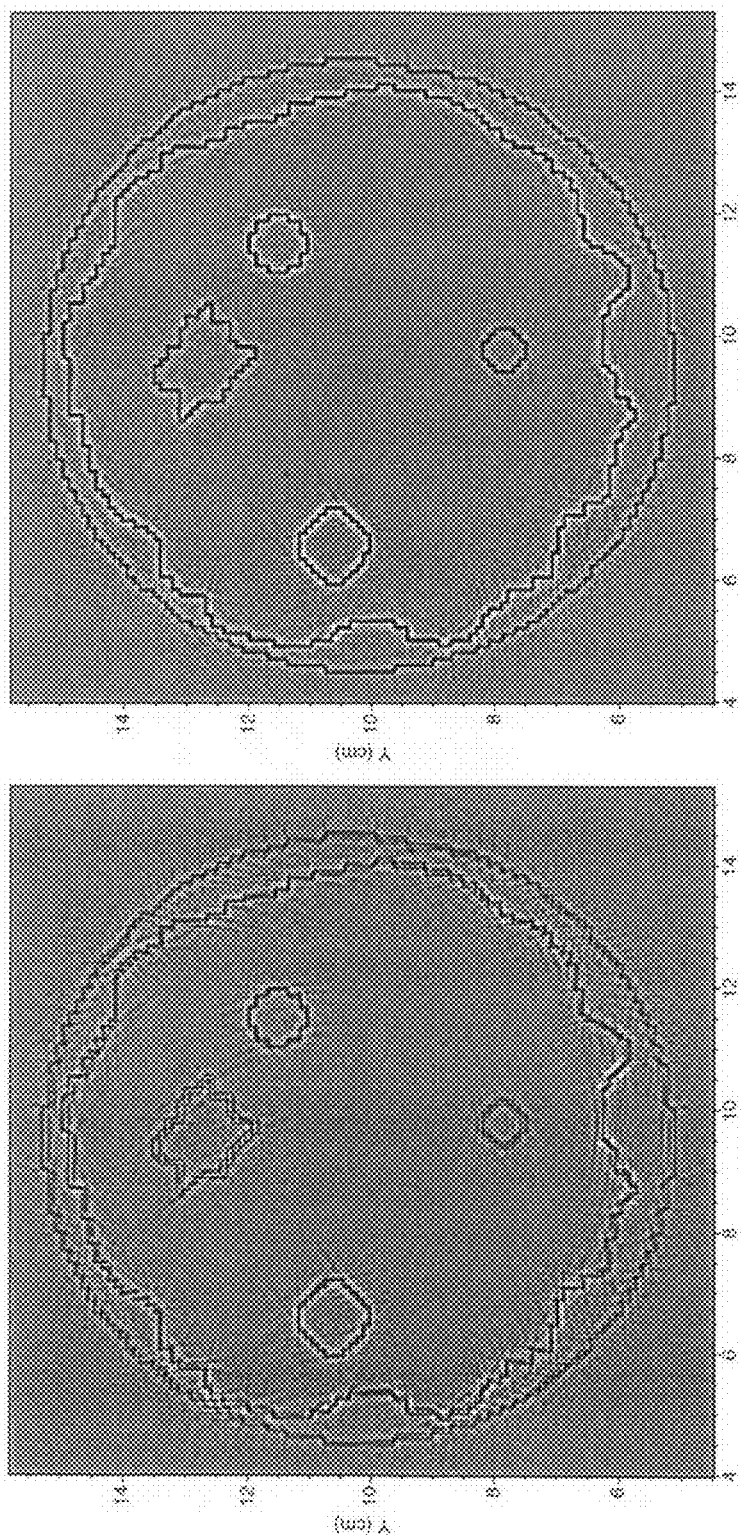

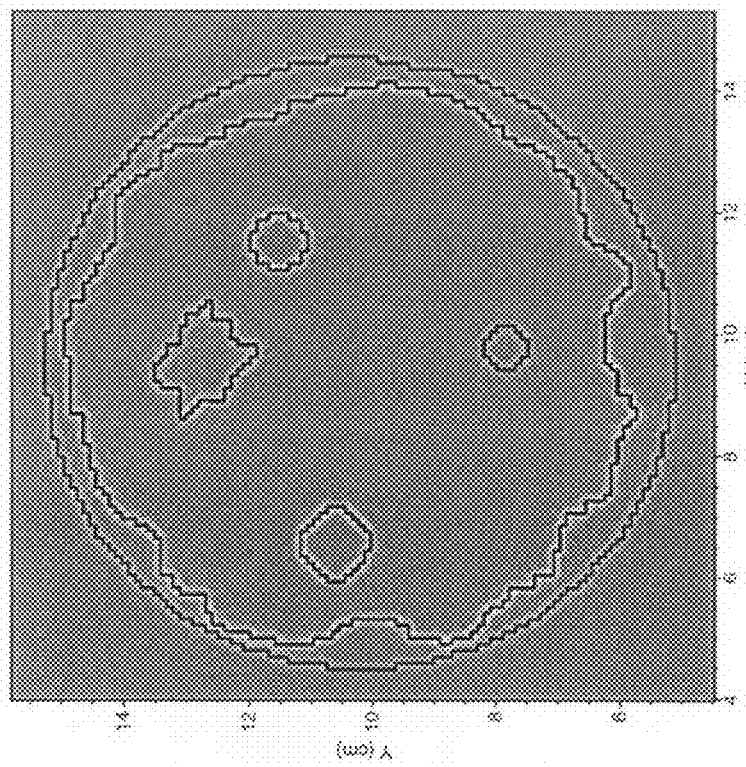
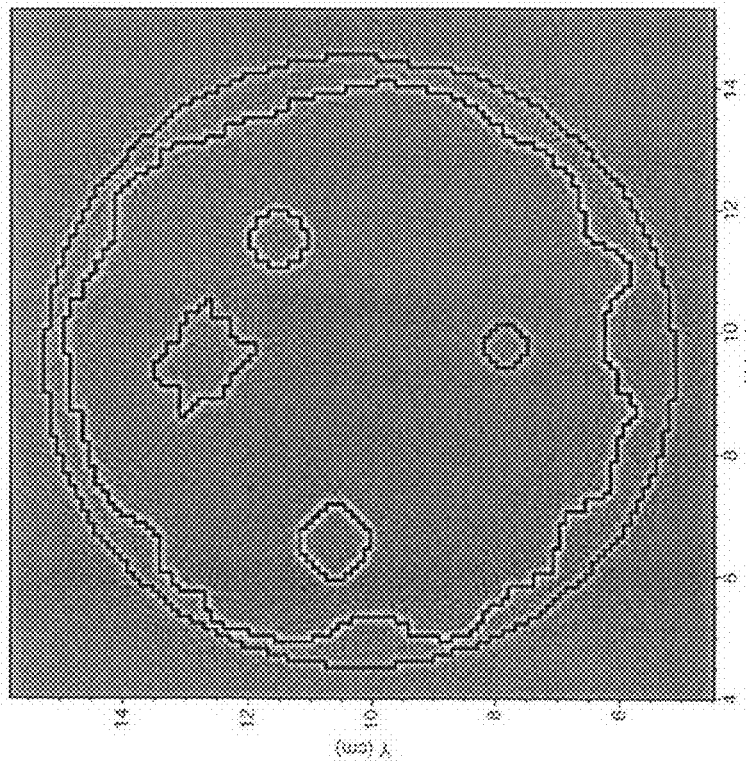
FIG. 13D
FIG. 13C

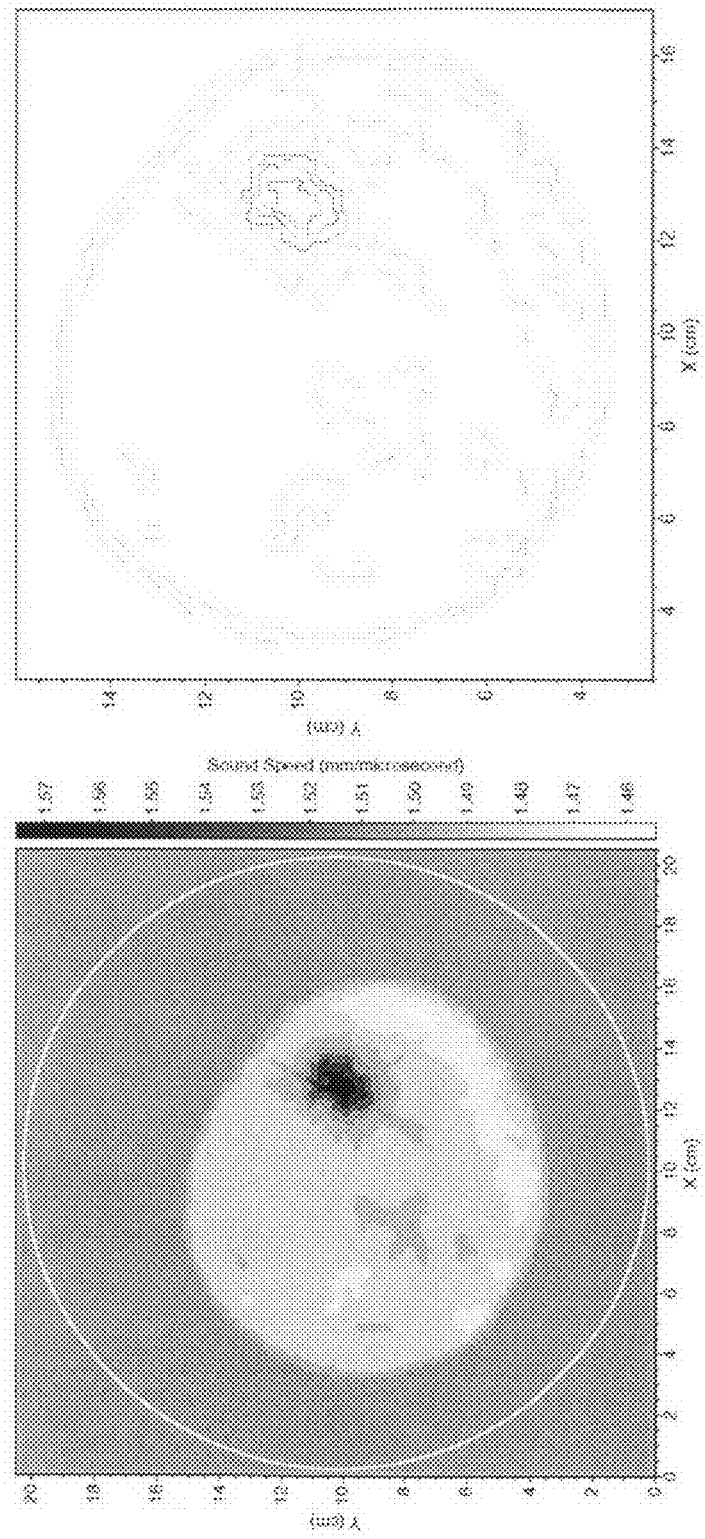

US 8,568,318 B2

HIGH-RESOLUTION WAVE-THEORY-BASED ULTRASOUND REFLECTION IMAGING USING THE SPLIT-STEP FOURIER AND GLOBALLY OPTIMIZED FOURIER FINITE-DIFFERENCE METHODS

CROSS-REFERENCE TO RELATED APPLICATIONS

This application claims priority from U.S. provisional patent application Ser. No. 60/901,903 filed on Feb. 16, 2007, incorporated herein by reference in its entirety.

STATEMENT REGARDING FEDERALLY SPONSORED RESEARCH OR DEVELOPMENT

This invention was made with Government support under Contract No. DE-AC52-06NA25396, awarded by the Department of Energy. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to ultrasound imaging, and more particularly to improving ultrasound image quality using Fourier finite difference methods.

2. Description of Related Art

Ultrasonic imaging is used in a wide variety of medical and clinical applications. Image formation in ultrasonography is typically provided in response to analysis of the time-of-flight and the angle of incidence of the reflected ultrasound signals. Ultrasound imaging is the second most often utilized imaging modality in medicine. However, due to poor image quality and resolution its use is typically limited to that of a complimentary imaging technique used in combination with other major imaging modalities such as X-ray imaging. Current clinical ultrasound reflection imaging methods and systems utilize a homogeneous model for reflectivity reconstruction and a ray approximation of ultrasound waves. These current methods generate ultrasound images which are noisy and contain numerous speckles.

Accordingly a need exists for a system and method which improves both the image quality and resolution of ultrasound reflection imaging, such as for use in clinical applications. These needs and others are met within the present invention, which overcomes the deficiencies of previously developed ultrasound imaging systems and methods.

BRIEF SUMMARY OF THE INVENTION

The methods and systems described within the present invention are directed at significantly improving both image quality and resolution of ultrasound imaging. One object of the invention is to make this imaging modality feasible for use as a primary imaging technique for early breast cancer detection and diagnosis.

Current clinical ultrasound reflection imaging is based on the use of a homogeneous model for reflectivity reconstruction, within which ray approximation of ultrasound waves is utilized. In the present invention it has been recognized that the use of these ray techniques cannot account for ultrasound scattering by tissue heterogeneities, which results in the generation of noisy and speckled ultrasound images.

Methods and systems of the present invention overcome the shortcomings of these ray techniques to achieve high-resolution ultrasound reflection imaging in response to the use of split-step Fourier and globally optimized Fourier finite-difference methods.

The invention is amenable to being embodied in a number of ways, including but not limited to the following descriptions.

One embodiment of the invention can be generally described as a method of ultrasound reflective image reconstruction for waveforms generated within an ultrasound imaging device, comprising: (a) receiving a heterogeneous sound-speed model of a tissue; (b) receiving ultrasonic waveform information in response to reflection data for a tissue region being tested; (c) reconstructing a reflection image using a split-step Fourier transform propagator configured for recursive inward continuation of ultrasonic wavefields in the frequency-space and frequency-wave number domains; (d) applying a first phase-shift term to the ultrasonic waveform information in the frequency-wave number domain for propagation in a reference medium; and (e) applying a second phase-shift term to the ultrasonic waveform information in the frequency-space domain to approximately compensate for ultrasonic scattering effects of heterogeneities within the tissue region.

One embodiment of the invention can be generally described as a method of ultrasound reflective image reconstruction for waveforms generated within an ultrasound imaging device, comprising: (a) receiving a heterogeneous sound-speed model of a tissue from tomography; (b) receiving ultrasonic waveform information in response to reflection data for a tissue region being tested; (c) reconstructing a reflection image using a split-step Fourier transform propagator configured for recursive inward continuation of ultrasonic wavefields in the frequency-space and frequency-wave number domains by, (c)(i) Fourier transforming of acoustic wavefield $U(x, z; \omega)$ with respect to x, (c)(ii) applying a phase-shift term $e^{-ik_z \Delta z}$ to the wavefield in the frequency-wave number $(\omega-k_x)$ domain, where $k_z = \sqrt{k_0^2 - k_x^2}$ with $k_0 = \omega/v_0$, and $k_x$ is the wave number along the x-coordinate, (c)(iii) inverse Fourier transformation of the resulting wavefield into the frequency-space $(\omega-x)$ domain, and (c)(iv) applying a phase-shift term $e^{-i\omega(s-s_0)}$ to approximately compensate for ultrasonic scattering effects of heterogeneities to generate the extrapolated acoustic wavefield.

One embodiment of the invention can be generally described as an apparatus for reconstructing reflective ultrasound images for waveforms generated within an ultrasound imaging device, comprising: (a) means for receiving a plurality of ultrasound waveforms from an ultrasound transducer apparatus (transmitter-receiver device) directed for reflection from a tissue; (b) a computer processor and memory coupled to the means; (c) programming executable on the processor for, (c)(i) receiving a heterogeneous sound-speed model of a tissue, (c)(ii) receiving ultrasonic waveform information in response to reflection data for a tissue region being tested, (c)(iii) reconstructing a reflection image using a split-step Fourier transform propagator configured for recursive inward continuation of ultrasonic wavefields in the frequency-space and frequency-wave number domains, (c)(iv) applying a first phase-shift term to the ultrasonic waveform information in the frequency-wave number domain for propagation in a reference medium, and (c)(v) applying a second phase-shift term to the ultrasonic waveform information in the frequency-space domain to approximately compensate for ultrasonic scattering effects of heterogeneities within the tissue region.

One embodiment of the invention can be generally described as a computer-readable media executable on a computer apparatus configured for reconstructing reflective ultrasound images for waveforms generated within an ultrasound imaging device, comprising: (a) a computer readable media containing programming executable on a computer processor configured for processing ultrasound waveforms in response to receiving a plurality of entire ultrasound waveforms from an ultrasound transducer device which directed reflections from a tissue under test; (b) the programming executable on the processor is configured for, (b)(i) receiving a heterogeneous sound-speed model of a tissue from tomography, (b)(ii) receiving ultrasonic waveform information in response to reflection data for a tissue region being tested, (b)(iii) reconstructing a reflection image using a split-step Fourier transform propagator configured for recursive inward continuation of ultrasonic wavefields in the frequency-space and frequency-wave number domains, (b)(iv) applying a first phase-shift term to the ultrasonic waveform information in the frequency-wave number domain for propagation in a reference medium, and (b)(v) applying a second phase-shift term to the ultrasonic waveform information in the frequency-space domain to approximately compensate for ultrasonic scattering effects of heterogeneities within the tissue region.

The present invention provides a number of beneficial aspects which can be implemented either separately or in any desired combination without departing from the present teachings.

An aspect of the invention is a technique for reducing noise and/or increasing resolution of ultrasound reflection imaging.

Another aspect of the invention is an ultrasound imaging method which is based on wave theory, instead of ray theory which is an asymptotic approximation of wave theory.

Another aspect of the invention is an ultrasound imaging method which utilizes entire ultrasound waveforms rather than time-of-flights for reflectivity reconstruction.

Another aspect of the invention is an ultrasound imaging method which utilizes a heterogeneous sound-speed model obtained from ultrasound tomography for imaging.

Another aspect of the invention is an ultrasound imaging method which properly accounts for ultrasound scattering from tissue heterogeneities.

Another aspect of the invention is an ultrasound imaging method which properly accounts for ultrasound scattering from heterogeneities within tissues being imaged.

A still further aspect of the invention is an ultrasound imaging method which is both robust and computationally efficient.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 13A-13D are images comparing reconstructed reflection images and ultrasound pulse-echo imaging using the split-step Fourier propagator, according to aspects of the present invention.

FIG. 15A-15B are images of numerical breast phantom and associated reflectivity of the phantom, in which the phantom contains heterogeneous breast tissues which are imaged according to aspects of the present invention.

DETAILED DESCRIPTION OF THE INVENTION

Figure 1:
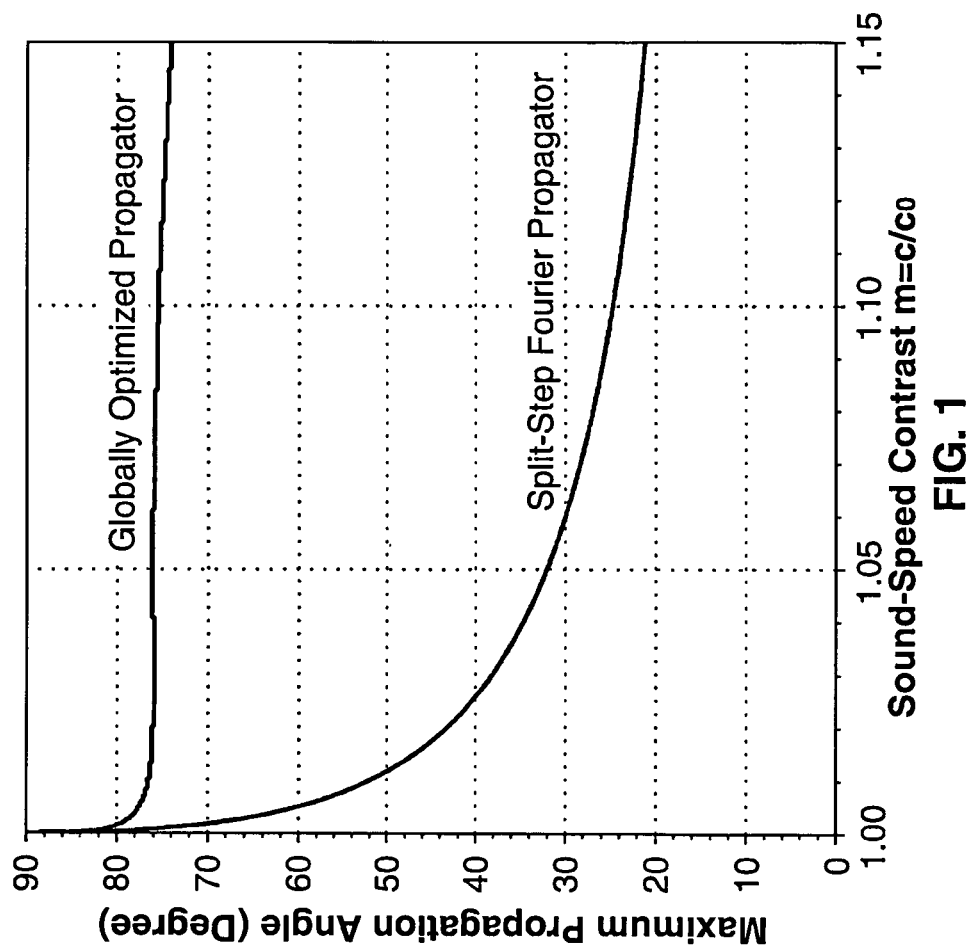
FIG. 1 is a graph of maximum propagation angle versus sound-speed contrast for the optimized propagator and the split-step Fourier propagator according to an aspect of the present invention.

Referring more specifically to the drawings, for illustrative purposes the present invention is embodied in the apparatus generally shown in FIG. 1, and FIG. 3 through FIG. 21. It will be appreciated that the apparatus may vary as to configuration and as to details of the parts, and that the method may vary as to the specific steps and sequence, without departing from the basic concepts as disclosed herein.

Section A

1. Introduction

To achieve high-resolution ultrasound reflection imaging it is essential to properly account for ultrasound scattering from heterogeneities within tissues being imaged, such as of the breast. A reflectivity image reconstruction method is needed which is capable of accurately handling ultrasound scattering. The teachings herein describe wave-theory-based methods for high-resolution reflectivity image reconstruction.

Ultrasound wave propagation in organic tissues, in particular breast or other human tissues, is governed by the acoustic-wave equation, which can be decomposed into two one-way wave equations describing wave propagation in opposite directions. One of these one-way wave equations in the frequency-space domain is given by:

$$\frac{\partial U(x, z; \omega)}{\partial z} = -iQ(x, z; \omega)U(x, z; \omega), \quad (1)$$

where U is the ultrasound pressure wavefield and the operator Q is defined by:

$$Q \equiv \sqrt{\frac{\omega^2}{c^2(x, z)} + \frac{\partial^2}{\partial x^2}} = \frac{\omega}{c(x, z)}R \quad (2)$$

where $\omega$ is the circular frequency, $(x, z)$ is the space location, c is the sound speed, and R is the square-root operator given by:

$$R \equiv \sqrt{1 - X^2} \text{ with} \quad (3)$$

$$X^2 \equiv -\frac{c^2}{\omega^2}\frac{\partial^2}{\partial x^2} \quad (4)$$

The formal solution of Eq. (1) is:

$$U(x,z+\Delta z;\omega) = \exp\{-i\int Qdz\}U(x,z;\omega) \quad (5)$$

which extrapolates the ultrasound wavefield U from the depth level at z to the next depth level at $z+\Delta z$.

The square-root operator R can be expanded in the form:

$$R \approx 1 - \frac{aX^2}{1 - bX^2}, \quad (6)$$

where a and b are free coefficients. The difference between operator Q, given by Eq. (2) and that in a background medium with a sound speed of $c_0(z)$ is:

$$D = \frac{\omega}{c}\sqrt{1 - X^2} - \frac{\omega}{c_0}\sqrt{1 - X_0^2} \quad (7)$$

where $X_0^2$ is given by:

$$X_0^2 = -\frac{c_0^2}{\omega^2}\frac{\partial^2}{\partial x^2} = \frac{X^2}{m^2} \quad (8)$$

where the sound-speed contrast $m(x,z)=c(x,z)/c_0(z)$ is the reciprocal of the refraction index. Making use of Eq. (6), Eq. (7) the following approximation is obtained:

$$D \approx \left(\frac{\omega}{c} - \frac{\omega}{c_0}\right) - \frac{\omega}{c_0}\frac{a(m-1)X_0^2}{1 - b(1 + m^2)X_0^2} \quad (9)$$

Therefore, Eq. (2) can be approximated by:

$$Q \approx \sqrt{\left(\frac{\omega^2}{c_0^2} + \frac{\partial^2}{\partial x^2}\right)} + \frac{\omega}{c_0}\left(\frac{1}{m} - 1\right) - \frac{\omega}{c_0}\frac{a(m-1)X_0^2}{1 - b(1 + m^2)X_0^2} \quad (10)$$

Ultrasound reflection imaging using the formal solution (5) with the first two terms of Eq. (10) is the split-step Fourier method.

One major advantage of the split-step Fourier method is that it is purely based on the Fourier transform, and therefore, the numerical dispersion is minimized. When using an assumption of uniform sound-speed for image reconstruction ($v=v_0$), the method leads to the phase-shift image reconstruction method.

The phase error is zero along the primary inward continuation direction. Then it increases with increasing the propagation angle relative to the primary direction. Substituting Eq. (10) into Eq. (5), and minimizing the phase error for the entire sound-speed perturbation range of the breast, yields the optimized values of coefficients a and b. The formal solution (5) with the third term of Eq. (10) is implemented using an implicit finite-difference scheme.

Ultrasound reflection imaging using the formal solution (5) with all three terms of Eq. (10) together with optimized free coefficients a and b is the globally optimized Fourier finite-difference method.

2. Experimental Results 2.1 Accuracy Analysis

Assuming the maximum sound-speed perturbation within the breast is 15%, FIG. 1 depicts the relationships of the maximum propagation angle within 1% of phase error versus the sound speed contrast for the optimized propagator and the split-step Fourier propagator. It shows that the optimized propagator can accurately handle much larger propagation angles than the split-step Fourier propagator, that is, it is much more accurate for large propagation angles compared with the split-step Fourier method for ultrasound propagation in heterogeneous human tissue.

2.2 Reflection Imaging of a Numerical Breast Phantom:

A numerical breast phantom derived from an in-vivo breast data is used to study the imaging capability of the inventive wave-theory-based ultrasound reflection imaging methods. The phantom contains a tumor with high sound-speeds. An ultrasound pulse with the second derivative of a Gaussian time function and a central frequency of 1 MHz is emitted from each transducer along a ring geometry surrounding the breast phantom.

Figure 2:
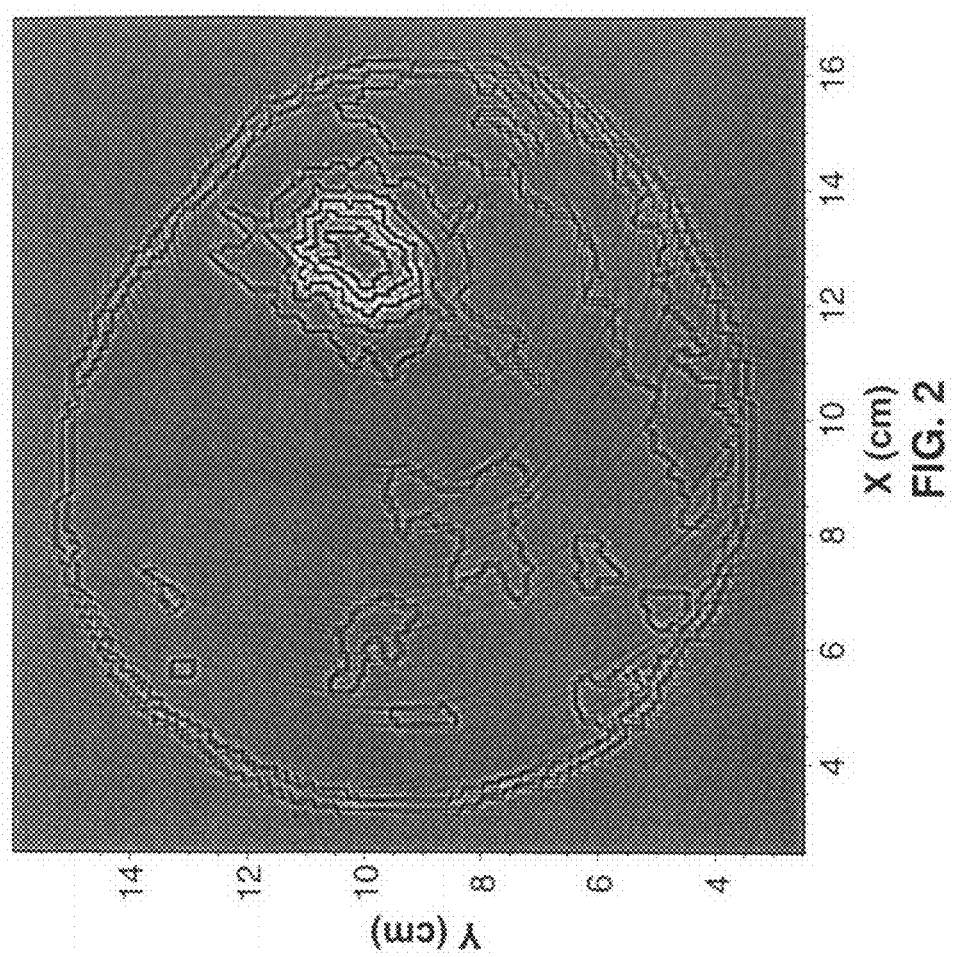
FIG. 2 is a conventional ultrasound reflection image of a numerical breast phantom, showing a substantial amount of image noise.

FIG. 2 is an ultrasound reflection image obtained using the phase-shift method with a homogeneous sound-speed model, like the conventional imaging method. It contains a lot of image artifacts because the phase-shift imaging method does not account for ultrasound scattering from the breast phantom heterogeneities.

Figure 3:
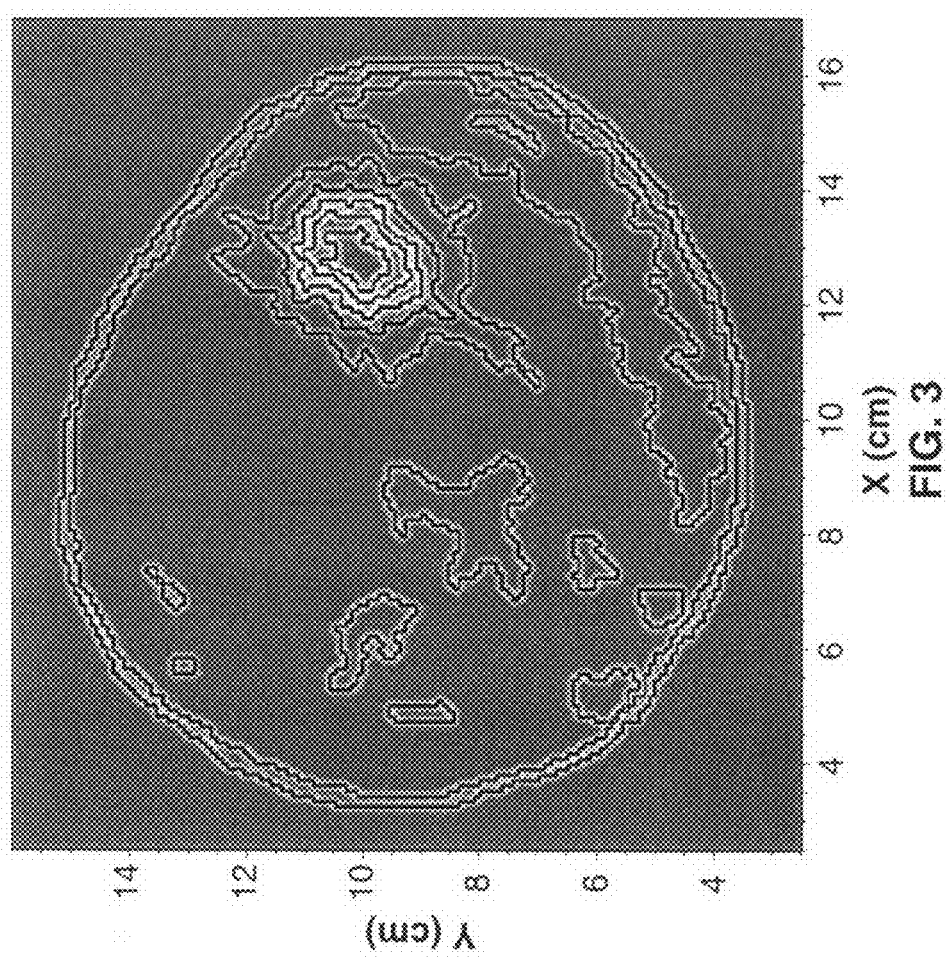
FIG. 3 is an ultrasound reflection image of a numerical breast phantom obtained according to an embodiment of the present invention.

FIG. 3 is an ultrasound reflection image of a numerical breast phantom obtained using the inventive globally optimized Fourier finite-difference method with a heterogeneous sound-speed model for image reconstruction. The same data that was imaged in FIG. 2 is processed using an inventive optimized reflection imaging method for reflectivity reconstruction to create the image output of FIG. 3. A heterogeneous sound-speed model of the phantom is used for image reconstruction. The resulting image shown FIG. 3 contains much fewer image noises and has much higher image resolution than FIG. 2. This demonstrates the vastly improved imaging capability of the inventive wave-theory-based ultrasound reflection imaging methods.

Section B

Section A provided a description and summarization of aspects of the invention, while the following two sections (Sections B and C) describe aspects of the invention in large part from the original descriptions. It should be appreciated that many of the equations and figures used in Sections B and C may duplicate those found in Section A. Figure numbering is continued from Section A, but equation numbering is restarted for each of Sections B and C to provide consistency with the original texts. Reference citation numbers are retained separately for each Section B and C to provide additional information.

3. Section B: Introduction

Properly accounting for ultrasound scattering from heterogeneities within tissue being examined, such as the breast, is essential toward providing high resolution ultrasound imaging. This requires a reflectivity image reconstruction method capable of accurately handling ultrasound scattering. The examples described herein are in reference to ultrasound imaging within breast tissue. An optimized ultrasound-wave propagator is described for reflectivity image reconstruction using pulse-echo ultrasound signals. The method is based on a solution of one-way wave equation and recursive inward continuation of ultrasound wavefields in the frequency-space and frequency-wave number domains using a heterogeneous sound-speed model of the breast obtained from tomography. It minimizes ultrasound phase errors during wavefield inward continuation while maintaining the advantage of high computational efficiency. Pulse-echo ultrasound imaging tests for a numerical breast phantom demonstrate that the optimized inventive method has the potential to improve the reliability and accuracy of reflection mode ultrasound breast imaging, and ultrasound imaging in general.

Ultrasonography uses pulse-echo ultrasound for imaging and is a common modality for breast cancer diagnosis. In addition, ultrasound breast imaging is one of the most promising screening tools as an alternative to x-ray mammography [9]. The primary limitation of ultrasonography is that ultrasound images contain a great deal of image noise. This limitation is mainly caused by ultrasound scattering from breast heterogeneities. Sound speeds and densities of breast tissue are inhomogeneous, and those of tumors are different from the surrounding tissues. These differences in mechanical properties result in ultrasound scattering, particularly in dense breasts. With the development of new circular ultrasound arrays for clinical breast imaging [6, 2, 10, 1], heterogeneous sound-speed models of the breast can be accurately obtained using ultrasound tomography [5, 7, 8]. Reflectivity image reconstruction can be significantly improved by using the heterogeneous sound-speed models for imaging. The split-step Fourier propagator was recently used for ultrasound pulse-echo imaging to approximately account for ultrasound scattering [4]. The method is computationally much more efficient than that based on finite difference time-domain wave-equation method [3].

An optimized ultrasound-wave propagator is described for ultrasound reflectivity image reconstruction using a solution for one-way wave equations in heterogeneous media, which is optimized for the sound-speed perturbation range of the tissue (e.g., breast) to minimize ultrasound phase errors during wavefield inward continuation. The method performs one additional step of ultrasound scattering compensation during each recursive step of inward continuation of ultrasound wavefields, in addition to the split-step Fourier implementation. It significantly improves imaging accuracy compared to the split-step Fourier method while it has much higher computational efficiency than the finite difference-based imaging method. Synthetic ultrasound pulse-echo data is used by way of example for a numerical breast phantom to demonstrate the improved imaging capability of our optimized imaging method.

4. Optimized Propagator

Ultrasound wave propagation in the breast is governed by the acoustic-wave equation, which can be decomposed into two one-way wave equations describing wave propagation in opposite directions. One of these one-way wave equations in the frequency-space domain is given by:

$$\frac{\partial U(x, z; \omega)}{\partial z} = -iQ(x, z; \omega)U(x, z; \omega), \quad (1)$$

where U is the pressure and the operator Q is defined by:

$$Q \equiv \sqrt{\frac{\omega^2}{c^2(x, z)} + \frac{\partial^2}{\partial x^2}} = \frac{\omega}{c(x, z)} R, \quad (2)$$

where $\omega$ is the circular frequency, (x,z) is the space location, c is the sound speed, and R is the square-root operator given by:

$$R \equiv \sqrt{1-X^2},\quad (3)$$

with $$X^2 \equiv -\frac{c^2}{\omega^2}\frac{\partial^2}{\partial x^2}. \quad (4)$$

The formal solution of Eq. (1) is:

$$U(x,z+\Delta z;\omega)=\exp\{-i\int Q dz\}U(x,z;\omega), \quad (5)$$

which extrapolates the ultrasound wavefield U from the depth level at z to the next depth level at $z+\Delta z$. The square-root operator R is expanded in the form:

$$R \approx 1 - \frac{aX^2}{1-bX^2}, \quad (6)$$

where a and b are free coefficients. The difference between operator Q, given by Eq. (2) and that in a background medium with a sound speed of $c_0(z)$ is:

$$D = \frac{\omega}{c}\sqrt{1-X^2} - \frac{\omega}{c_0}\sqrt{1-X_0^2}, \quad (7)$$

where $X_0^2$ is given by:

$$X_0^2 = -\frac{c_0^2}{\omega^2}\frac{\partial^2}{\partial x^2} = \frac{X^2}{m^2} \quad (8)$$

where the sound-speed contrast $m(x,z)=c(x,z)/c_0(z)$ is the reciprocal of the refraction index. Making use of Eq. (6) and Eq. (7) can be approximated as:

$$D \approx \left(\frac{\omega}{c}-\frac{\omega}{c_0}\right) - \frac{\omega}{c_0}\frac{a(m-1)X_0^2}{1-b(1+m^2)X_0^2}. \quad (9)$$

Therefore, Eq. (2) can be approximated by:

$$Q \approx \sqrt{\left(\frac{\omega^2}{c_0^2}+\frac{\partial^2}{\partial x^2}\right)} + \frac{\omega}{c_0}\left(\frac{1}{m}-1\right) - \frac{\omega}{c_0}\frac{a(m-1)X_0^2}{1-b(1+m^2)X_0^2} \quad (10)$$

The formal solution of Eq. (5) with the first two terms of Eq. (10) is the split-step Fourier operator [4]. The formal solution of Eq. (5) with the third term of Eq. (10) is implemented using an implicit finite-difference scheme. The phase error is zero along the primary inward continuation direction. Then it increases with increasing propagation angle relative to the primary direction. Substituting Eq. (10) into Eq. (5) and minimizing the phase error for the entire sound-speed perturbation range of the breast, the optimized values of coefficients a and b are obtained. The resulting propagator is termed the globally optimized Fourier finite-difference propagator.

The relationships of the maximum propagation angle is within 1% of phase error versus the sound-speed contrast for the optimized propagator and the split-step Fourier propagator. Assuming the maximum sound-speed perturbation within the breast is 15%, FIG. 1 as previously discussed, depicts the relationships of the maximum propagation angle within 1% of phase error versus the sound-speed contrast for the optimized propagator and the split-step Fourier propagator. It shows that the optimized propagator can accurately handle much large propagation angles than the split-step Fourier propagator, that is, it is much more accurate for large propagation angles compared with the split-step Fourier propagator.

5. Numerical Pulse-Echo Imaging Examples

Figure 4:
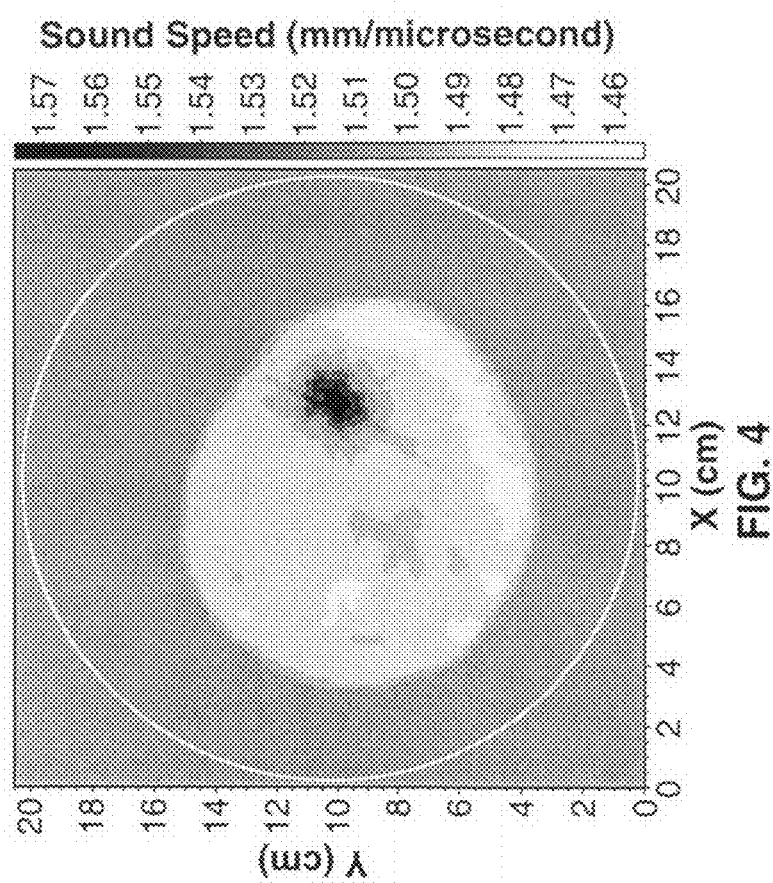
FIG. 4 is an image of a numerical breast phantom derived from sound-speed transmission tomography of an in-vivo breast dataset according to an aspect of the present invention.

FIG. 4 is an image of a numerical breast phantom derived from sound-speed transmission tomography of an in-vivo breast dataset, with the white solid circle indicating the location of the transducer ring. The numerical breast phantom of the figure is used to study the pulse-echo imaging capability of described optimized propagator, and the phantom is derived from in-vivo breast tomography, and the region with high sound-speed is a tumor. An ultrasound pulse with the second derivative of a Gaussian time function and a central frequency of 1 MHz is emitted from each transducer along the white solid circle, and ultrasound pulse-echo signals are recorded by the same transducer. Numerical data are generated using a finite difference time-domain acoustic-wave equation in heterogeneous media.

Figure 5A:
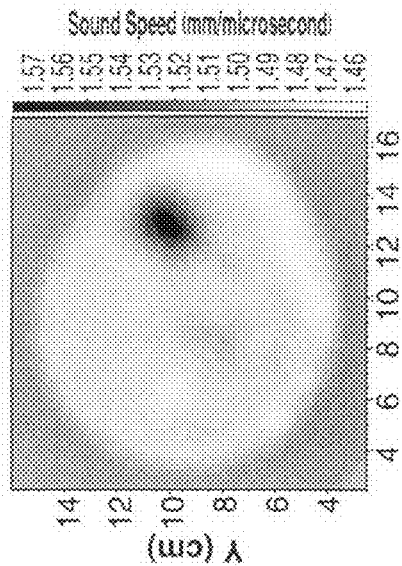
FIG. 5A-5D are images of reflectivity and absolute values of sound-speed discrepancies, respectively, according to aspects of the present invention.
Figure 5B:
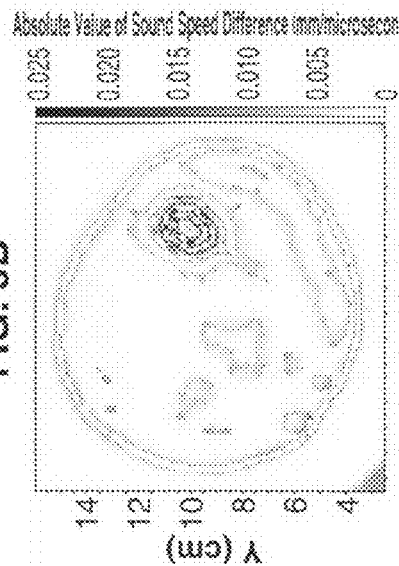
Figure 5C:
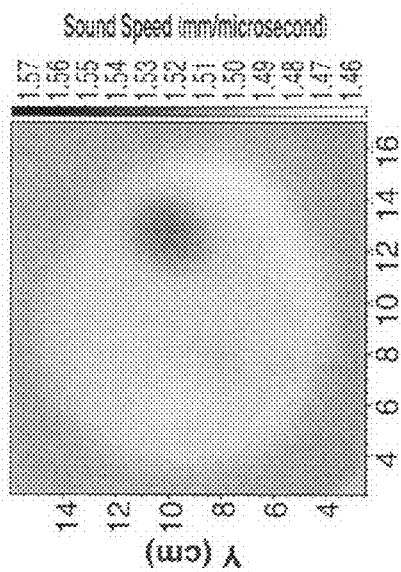
Figure 5D:
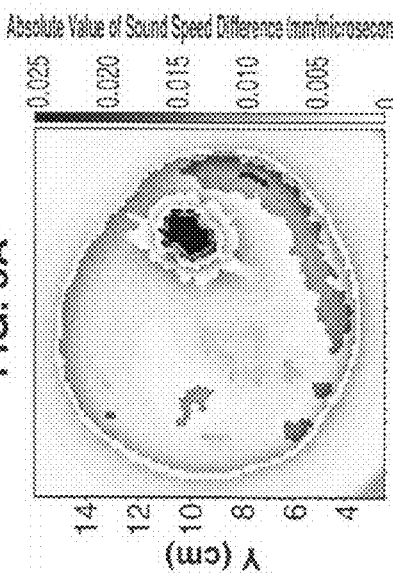

FIG. 5A-5D is a set of images relating sound-speed transmission tomography results of the numerical breast phantom. FIG. 5A-5B are reflectivity image reconstructions. FIG. 5A illustrates imaging in response to one iteration, while FIG. 5B illustrates imaging in response to ten iterations. FIG. 5C-5D depict absolute values of sound-speed discrepancies. The figures depict different sound-speed transmission tomography results of the numerical breast phantom, together with their absolute values of sound-speed discrepancies, that is, the absolute values of the differences between FIGS. 5A-5B and the correct sound speed in FIG. 4. The discrepancies and/or errors of the tomography result with ten iterations are considerably smaller than that with one iteration. In addition, the largest discrepancies arise in the tumor region, as shown in FIGS. 5C and 5D.

Figure 6A:
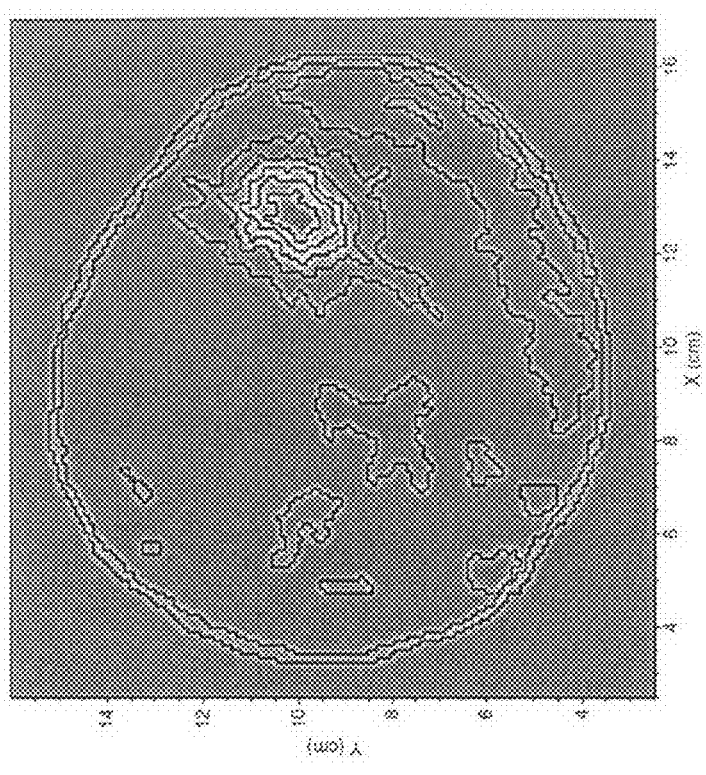
FIG. 6A-6B are images of reflectivity for phantom reconstructions using the optimized propagator according to aspects of the present invention.
Figure 6B:
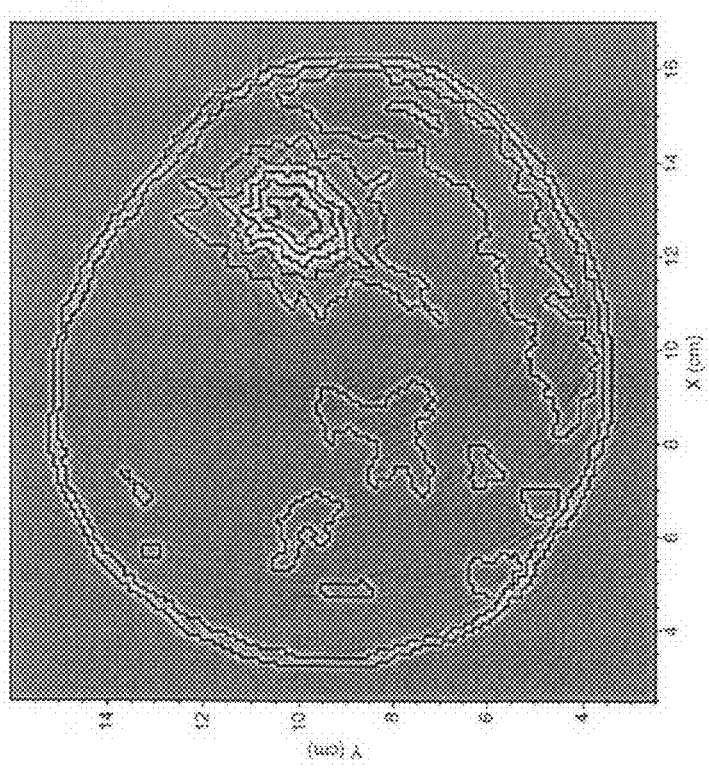

FIG. 6A-6B are reflectivity images of the numerical phantom reconstructed using the optimized propagator and the heterogeneous sound-speed models in FIG. 5A-5B. FIG. 6A contains significantly more image noise than that of FIG. 6B. In addition, the images in the tumor region in FIG. 6A are not well reconstructed, while those in FIG. 6B are well imaged. FIG. 6A demonstrates that large sound-speed discrepancies as shown in FIG. 5C can result in significant image artifacts in reflectivity images, because ultrasound scattering is not properly accounted for during reflectivity image reconstruction.

Reflectivity image artifacts caused by propagator inaccuracy and sound-speed discrepancies are important considerations. High-resolution and high-quality ultrasound images can be obtained by properly accounting for ultrasound scattering during reflectivity image reconstruction. This requires an accurate wave propagator and an accurate sound-speed model. Reflectivity image artifacts (including image noise, incorrect image location and amplitudes) are caused not only by propagator inaccuracy, but also by the discrepancies and/or errors in the sound-speed model used for image reconstruction. Low ultrasound data quality and improper transducer distribution can also contribute to image artifacts; although for the sake of simplicity neither of these factors are included in this study.

Figure 7:
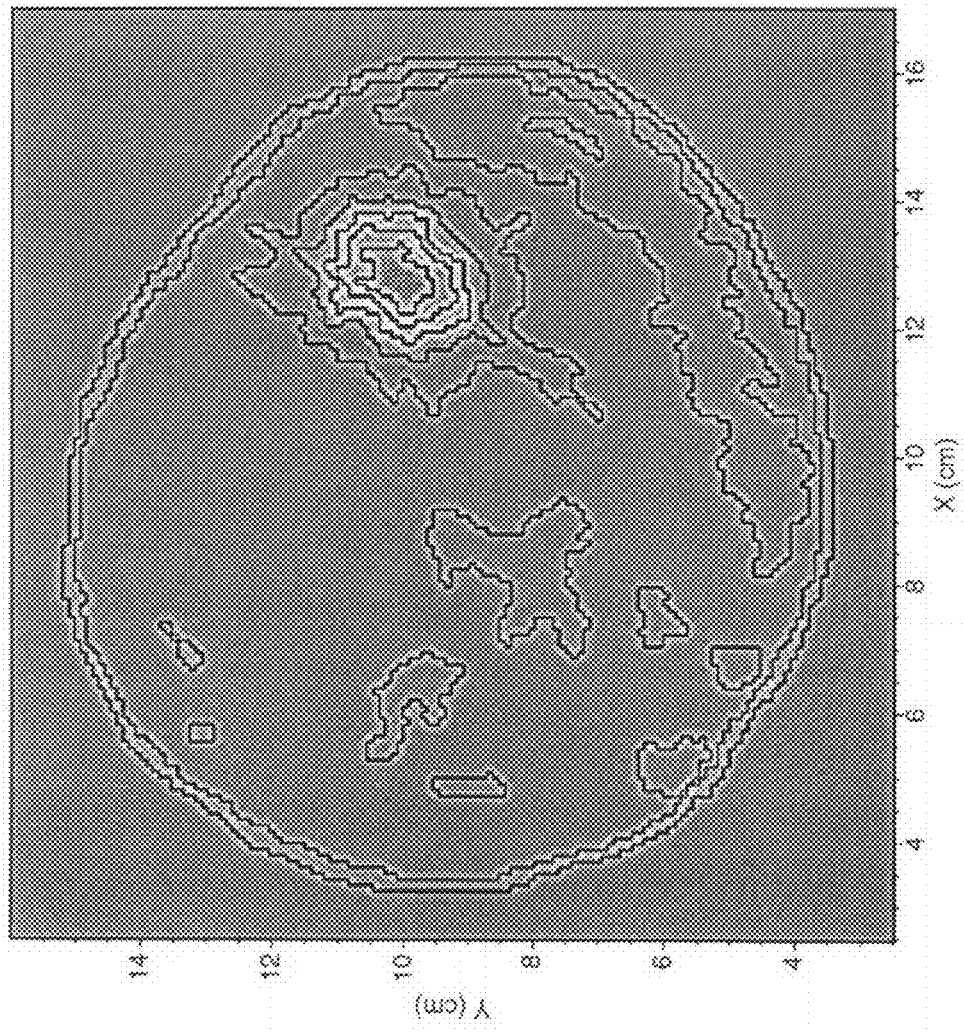
FIG. 7 is a reflectivity image reconstructed using the optimized propagator and used as a comparison standard.

FIG. 7 is a reflectivity image reconstructed using the optimized propagator and the correct sound speed of the breast phantom of FIG. 4. The figure does not contain any image artifacts caused by sound-speed discrepancies, wherein this image is utilized, by way of example, as an image comparison standard.

Figure 8A:
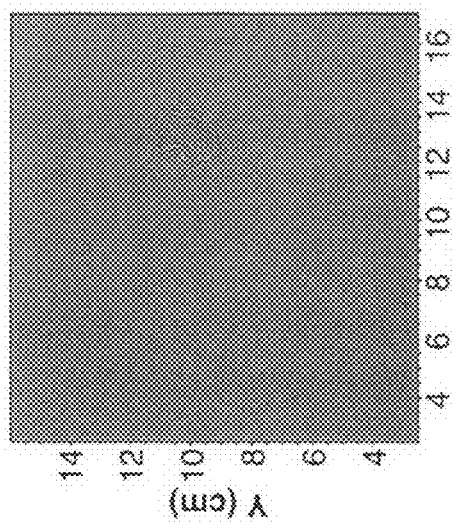
FIG. 8A-8D are images depicting the differences between reconstructed reflectivity images, according to aspects of the present invention.
Figure 8B:
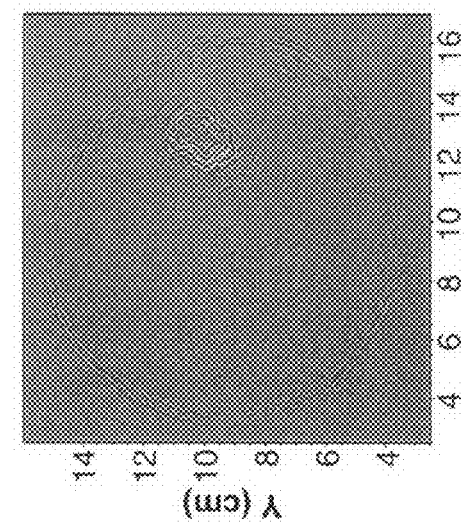
Figure 8C:
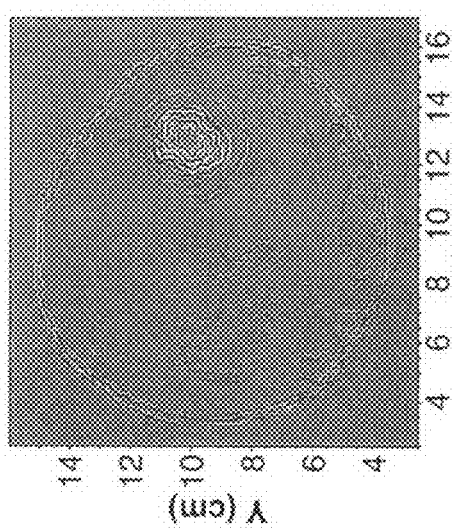
Figure 8D:
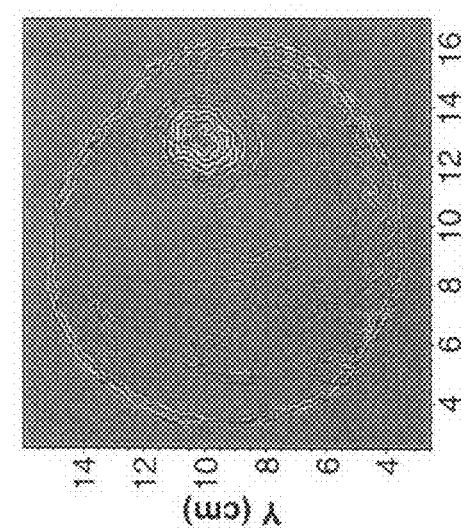

FIG. 8A-8D are comparative images so that the differences between different reconstructed reflectivity images can be compared with that of FIG. 7. The sound-speed model used in FIG. 8A and FIG. 8C is that in FIG. 5A, and that used in FIG. 8B and FIG. 8D is the one shown in FIG. 5B. Comparisons of FIG. 8B with FIG. 8A, and FIG. 8D with FIG. 8C, indicate that reflectivity image artifacts decrease with increasing accuracy of the tomography sound-speed results. When the sound-speed discrepancy is large, the comparison of FIG. 8A and FIG. 8B indicates that reflectivity images are similar to one another no matter which propagator is used for image reconstruction. That is, image artifacts caused by the sound-speed discrepancy are much stronger than those caused by the propagator inaccuracy when the sound-speed discrepancy is large. When the sound-speed discrepancy is small, comparison of FIG. 8B and FIG. 8D show that image artifacts decrease with increasing propagator accuracy.

Figure 9A:
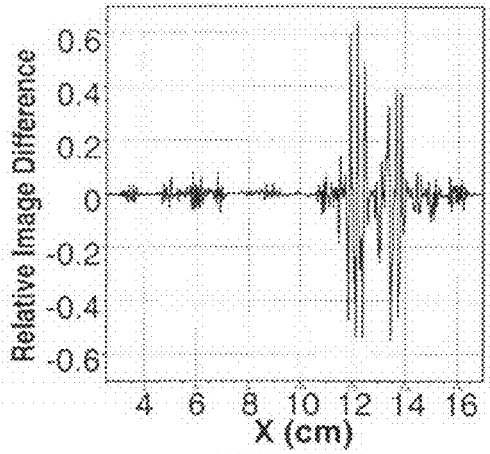
FIG. 9A-9E are images of signal differences across panel cross-sections, according to aspects of the present invention.
Figure 9B:
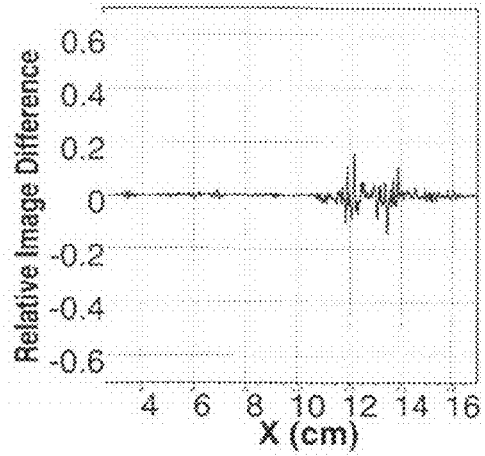
Figure 9C:
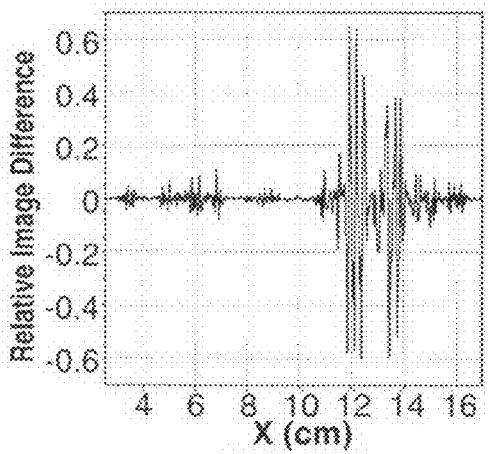
Figure 9D:
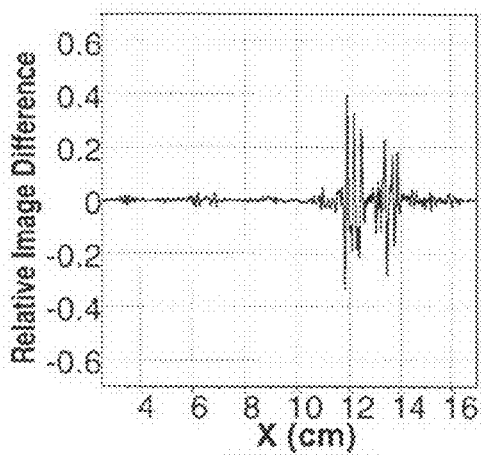
Figure 9E:
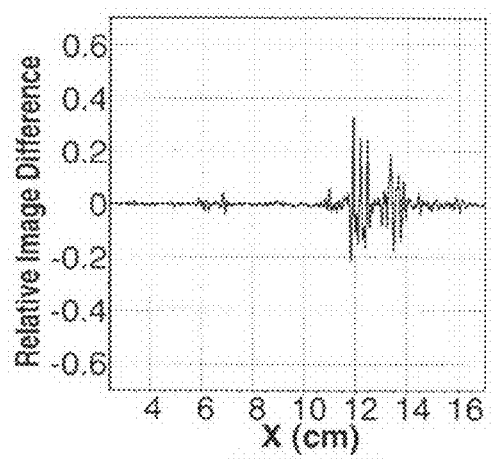

FIG. 9A-9E depict image differences across panel cross-sections. FIG. 9A-9D indicate, respectively, the relative image differences along the cross sections of the panels in FIG. 8A-8D at b=98 mm. FIG. 9E was obtained for an image using the split-step Fourier propagator and the correct sound speed of the phantom, compared with the image in FIG. 7.

Relative image differences in FIG. 9A-9E give a quantitative comparison of image artifacts. It can be seen that the most significant image artifacts occur around the tumor region. The difference between FIG. 9A and FIG. 9C is small and may be insignificant for most purposes. The image artifacts in FIG. 9E are caused by inaccuracy of the split-step Fourier propagator.

6. Section B: Conclusions

An optimized propagator is described for ultrasound reflectivity imaging and validated using ultrasound pulse-echo data for a numerical breast phantom. The propagator is optimized for the sound-speed perturbation range within the tissue being imaged, such as breast tissue.

The inventive optimized propagator is more accurate than the split-step Fourier method for handling ultrasound scattering in the heterogeneous breast. The importance of obtaining an accurate sound-speed model of the breast for reflectivity image reconstruction has been numerically demonstrated above. The inventive method can produce high-resolution and high-quality ultrasound reflectivity images using an accurate, heterogeneous sound-speed tomography model for image reconstruction.

7. Section B: References

[1] N. Duric, P. Littrup, LPoulo, A. Babkin, R. Pevzner, E. Holsapple, and O. Rama. Detection of breast cancer with ultrasound tomography: First results with the computerized ultrasound risk evaluation (cure) prototype. Med. Phys., 34:773-785, 2007.

[2] N. Duric, P. J. Littrup, A. Babkin, D. Chambers, S. Azevedo, A. Kalinin, R. Pevzner, M. Tokarev, E. Holsapple, O. Rama, and R. Duncan. Development of ultrasound tomography for breast imaging: Technical assessment. Med. Phys., 32:1375-1386, 2005.

[3] L. Huang, N. Duric, and P. Littrup. Breast imaging with time-reversed ultrasound. In S. Emelianov and W. F. Walker, editors, Proc. SPIE: Ultrasonic Imaging and Signal Processing, volume 6147, pages 156-167, Bellingham, Wash., 2006. SPIE.

[4] L. Huang and Y. Quan. Ultrasound pulse-echo imaging using the split-step fourier propagator. In S. Y. Emelianov and S. A. McAleavey, editors, Proc. SPIE: Ultrasonic Imaging and Signal Processing, volume 6513, Bellingham, Wash., 2007. SPIE.

[5] R. R. Leach Jr., S. G. Azevedo, J. G. Berryman, H. R. Bertete-Aguirre, S. H. Chambers, J. E. Mast, P. Littrup, N. Duric, S. A. Johnson, and F. Wuebbeling. Comparison of ultrasound tomography methods in circular geometry. In M. Insana and W. F. Walker, editors, Proc. SPIE: Ultrasonic Imaging and Signal Proceesing, volume 4687, pages 362-377, Bellingham, Wash., 2002. SPIE.

[6] S. J. Norton and M. Linzer. Ultrasonic reflectivity tomography: reconstruction with circular transducer arrays. Ultrasonic Imaging, 2:154-184, 1979.

[7] R. G. Pratt, L. Huang, N. Duric, and P. Littrup. Sound-speed and attenuation of the breast tissue using waveform tomography of transmission ultrasound data. In J. Hsieh and M. J. Flynn, editors, Proc. SPIE: Physics of Medical Imaging, volume 6510, Bellingham, Wash., 2007. SPIE.

[8] Y. Quan and L. Huang. Sound-speed tomography using firstarrival transmission ultrasound for a ring array. In S. Y. Emelianov and S. A. McAleavey, editors, Proc. SPIE: Ultrasonic Imaging and Signal Processing, volume 6513, Bellingham, Wash., 2007. SPIE.

[9] E. A. Sickles. Breast imaging: From 1965 to the present. Radiology, 215:1-16, 2000.

[10] R. C. Waag and R. J. Fedewa. A ring transducer system for medical ultrasound research. IEEE Trans. Ultrason. Ferroelectr. Freq. Control, 53:1707-1718, 2006.

Section C

8. Section C: Introduction

Ultrasonic reflection imaging has the potential to produce higher image resolution than transmission tomography, but imaging resolution and quality still need to be further improved for early cancer detection and diagnosis. An inventive ultrasound reflection image reconstruction method is described using the split-step Fourier propagator. The reconstruction method is based on recursive inward continuation of ultrasonic wavefields in the frequency-space and frequency-wave number domains. The inward continuation within each extrapolation interval consists of two steps. In the first step, a phase-shift term is applied to the data in the frequency-wave number domain for propagation in a reference medium. The second step consists of applying another phase-shift term to data in the frequency-space domain to approximately compensate for ultrasonic scattering effects of heterogeneities within the tissue being imaged, (e.g., breast tissue). Synthetic ultrasound pulse-echo data recorded around a ring for heterogeneous, computer-generated, numerical breast phantoms is used for studying the imaging capability of the method. By way of example and not limitation, the phantoms are derived from an experimental breast phantom and a sound-speed tomography image of in-vivo ultrasound breast data collected using a ring array. The heterogeneous sound-speed models used for pulse-echo imaging are obtained using a computationally efficient, first-arrival-time (time-of-flight) transmission tomography method. Tests are described on the inventive method which demonstrate that reflection image reconstruction using the split-step Fourier propagator with heterogeneous sound-speed models significantly improves image quality and resolution. In addition numerical verification of these spatial sampling criterion of wavefields is provided for a ring transducer array.

It should be appreciated, that although ultrasonic imaging is the second most often used imaging modality in medicine [1] its role is usually limited to compliment the other major imaging modalities such as x-ray imaging. It is therefore of significant importance to improve the image quality and resolution of ultrasonic imaging in order to make this imaging modality feasible, such as to enhance early breast cancer detection and diagnosis. Current limitations of ultrasonic imaging arise from commonly used linear transducer arrays that restrict the data acquisition aperture, and lack the ability to compensate for ultrasonic scattering effects during image reconstruction; thus resulting in low-resolution and noisy images. To alleviate the first limitation, several groups have developed ring transducer arrays to increase the data acquisition aperture. [2-9]

The recent technological advances in ring transducer arrays provide an opportunity to accurately obtain sound-speed tomography images of the breast. [10-13] Such images are normally smooth and the image resolution is low. An inventive ultrasound reflection image reconstruction method is described in this section which makes use of smooth sound-speed tomography results for wavefield inward continuation to improve image quality and resolution.

The wavefield extrapolation is carried out using the split-step Fourier propagator that has been used for modeling and imaging in other fields, [14-18] but has not yet been studied for medical ultrasound imaging. The image reconstruction capability of the split-step Fourier propagator for ultrasound breast imaging is studied herein by way of example using a ring array and computer-generated breast phantoms. The split-step Fourier propagator is based on the Fourier transform and phase shift in the frequency-wave number and frequency-space domains. Therefore, the split-step Fourier propagator minimizes the numerical dispersion and consequently reduces image artifacts. Reflection image reconstruction with the split-step Fourier propagator is computationally much more efficient than full wave-equation-based time-reversal image reconstruction, [19] but provides more accuracy than phase-shift image reconstruction. [20] Ultrasound reflection image reconstruction is demonstrated using the split-step Fourier propagator with heterogeneous sound-speed models to significantly improve image resolution and quality compared to phase-shift image reconstruction.

The sampling criterion of wavefields needed to image objects within a ring array has been recently developed. [21] A synthetic ultrasound pulse-echo dataset recorded by a ring array for a computer-generated breast phantom is utilized for numerically verifying the sampling criterion.

9. Split-Step Fourier Propagator

The acoustic-wave equation can be decomposed into two one-way wave equations describing wave propagation in opposite directions. The one-way wave equation in the frequency-space domain is given by:

$$\frac{\partial U(x,z;\omega)}{\partial z} = -i\sqrt{\frac{\omega^2}{v^2(x,z)} + \frac{\partial^2}{\partial x^2}}\, U(x,z;\omega,) = -iQ(x,z;\omega)U(x,z;\omega), \quad (1)$$

where (x,z) is the space position, w is the circular frequency, v is the sound speed, U is the acoustic wavefield, and the operator Q is defined by:

$$Q(x,z,\omega) \equiv \sqrt{\frac{\omega^2}{v^2(x,z)} + \frac{\partial^2}{\partial x^2}} = \sqrt{\frac{\omega^2}{v_0^2(z)} + \frac{\partial^2}{\partial x^2}} + \left\{\sqrt{\frac{\omega^2}{v^2(x,z)} + \frac{\partial^2}{\partial x^2}} - \sqrt{\frac{\omega^2}{v_0^2(z)} + \frac{\partial^2}{\partial x^2}}\right\} \quad (2)$$

with $v_0$ as a reference sound speed. Eq. (2) can be approximated by:

$$Q(x,z,\omega) \approx \sqrt{\frac{\omega^2}{v_0^2(z)} + \frac{\partial^2}{\partial x^2}} + \omega\left(\frac{1}{v(x,z)} - \frac{1}{v_0(z)}\right) = \sqrt{\frac{\omega^2}{v_0^2(z)} + \frac{\partial^2}{\partial x^2}} + \omega[s(x,z) - s_0(z)], \quad (3)$$

where the slowness $s=1/v$, and the reference slowness $s_0=1/v_0$. The formal solution of equation (1) is:

$$U(x,z+\Delta z;\omega) = \exp\{-i\int Q dz\} U(x,z;\omega) \quad (4)$$

which extrapolates the acoustic wavefield U from z to z+Δz.

Inward continuation of the wavefield from receiving transducers into the tissue (e.g., breast) using Eq. (4), together with Eq. (3), can be implemented with the following steps: (a) Fourier transform of acoustic wavefield U(x,z; ω) with respect to x; (b) Applying a phase-shift term $e^{-ik_z\Delta z}$ to the wavefield in the frequency-wave number (ω–$k_x$) domain, where $k_z=\sqrt{k_0^2-k_x^2}$ with $k_0=\omega/v_0$, and $k_x$ is the wave number along the x-coordinate; (c) Inverse Fourier transform of the resulting wavefield into the frequency-space (ω–x) domain; (d) Applying a phase-shift term $e^{i\omega(s-s_0)}$ to approximately compensate for ultrasonic scattering effects of heterogeneities. The resulting wavefield is the extrapolated acoustic wavefield. The wavefield inward continuation using the above procedure is termed the split-step Fourier (SSF) propagator. For ultrasound pulse-echo signals, the ultrasound propagation time from a transmitter to a scatterer, and then back to the transmitter/receiver, is twice the propagation time from the transmitter to the scatter. Therefore, a time sample interval that is half of that of the pulse-echo data is used for pulse-echo imaging to focus scattering wavefields back to scatterers. The image I(x,z) is obtained at time zero of back-propagated wavefields, and is calculated using:

$$I(x,z) = \int U(x,z;\omega)d\omega \quad (5)$$

One major advantage of the split-step Fourier method is that it is based on the Fourier transform, and therefore, numerical dispersion is minimized. When using an assumption of uniform sound-speed for image reconstruction ($v=v_0$), the method regresses to the phase-shift image reconstruction scheme. [20]

10. Imaging of a Phantom Derived from Experimental Breast Phantom

Two numerical breast phantoms are used to investigate the capability of the split-step Fourier propagator for reflection image reconstruction. An important advantage of using computer-generated phantoms in image-reconstruction studies is that the exact sound-speed model of the phantoms is known, and thus the reflection image reconstructed using the exact sound-speed provides an accurate standard ("gold standard") for image quality and resolution that could be achieved using a given image-reconstruction algorithm. Another advantage is that numerical phantoms can be easily altered to simulate different tissues (anatomies) and medical situations. It is currently difficult to study combinations of different medical situations of patients using clinical data.

Figure 10B:
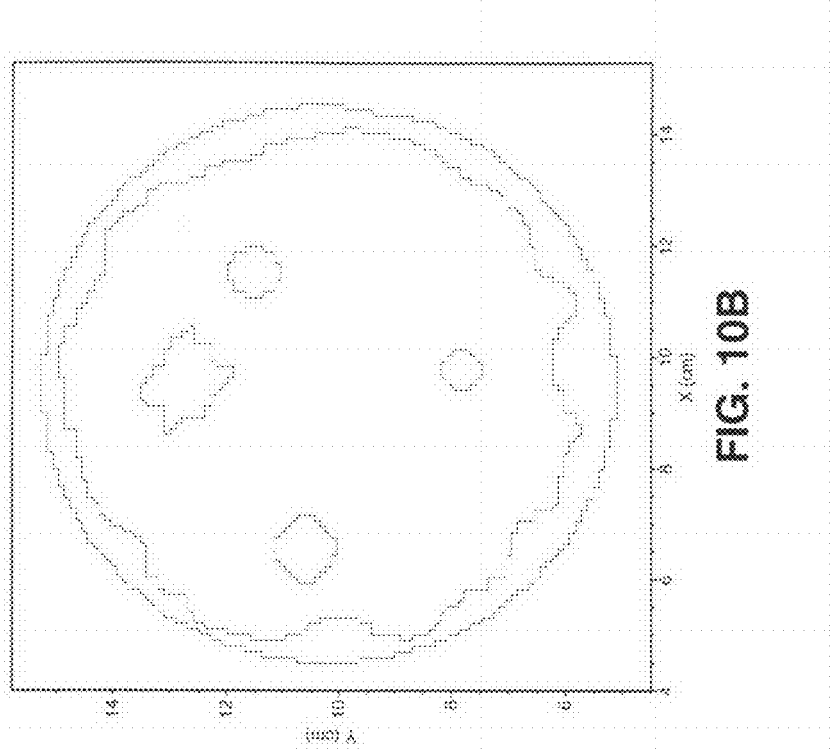
FIG. 10A-10B are images of a breast phantom containing two tumors showing numerical image and reflectivity, according to aspects of the present invention.
Figure 10A:
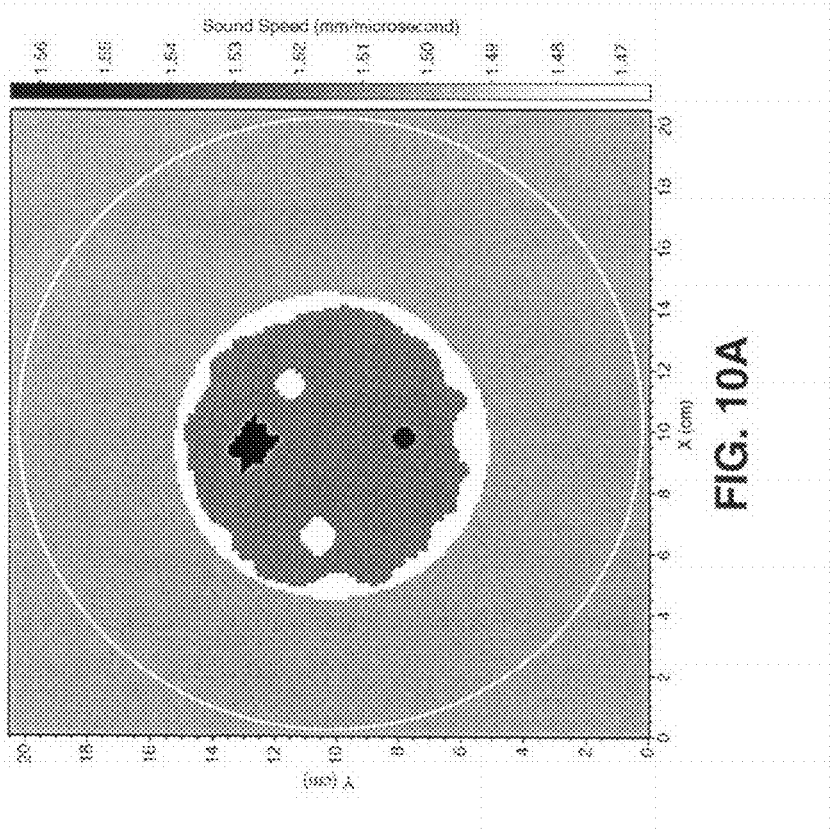

FIG. 10A-10B illustrate sound speed of a numerical breast phantom derived from an experimental breast phantom that contain two tumors with high sound-speeds, and two fatty tissues with low sound-speeds. FIG. 10A depicts the numerical breast phantom, while FIG. 10B depicts reflectivity of the phantom which shows where changes of acoustic impedances occur. The outer white solid circle in FIG. 10A is the ring array used to record synthetic pulse-echo data. The first numerical breast phantom shown in FIG. 10A-10B, contains four phantom breast masses, and is derived from an experimental breast phantom from the Karmanos Cancer Institute. It consists of a subcutaneous layer of fat, a faceted parenchyma, and two tumors with higher sound speeds and two fatty masses with lower sound speeds compared to the surrounding tissue. The larger tumor is more irregular than the other anomalies. The surfaces of all phantom breast masses in FIG. 10A are rough, resulting in a significant amount of ultrasound scattering. An enlarged display of reflectivity (normal reflection coefficient) within the phantom is given in FIG. 10B. The maximum value of reflectivity is 0.015. It would be ideal if reflection images would look like the reflectivity.

A finite-difference time-domain scheme is utilized for the acoustic-wave equation in heterogeneous media to generate ultrasound pulse-echo data for the numerical breast phantom in FIG. 10A. It is assumed that the densities of the phantom tissues are proportional to their sound speeds during the finite-difference calculation. The data is recorded across a plurality (e.g., 4096) transducers that are equally distributed around the ring shown as the white solid circle in FIG. 10A. The central frequency of the data is 1 MHz. By way of example, the data herein is for a ring array with a diameter of about 20 cm, and each transducer receives scattering signals emitted from itself.

Figure 11:
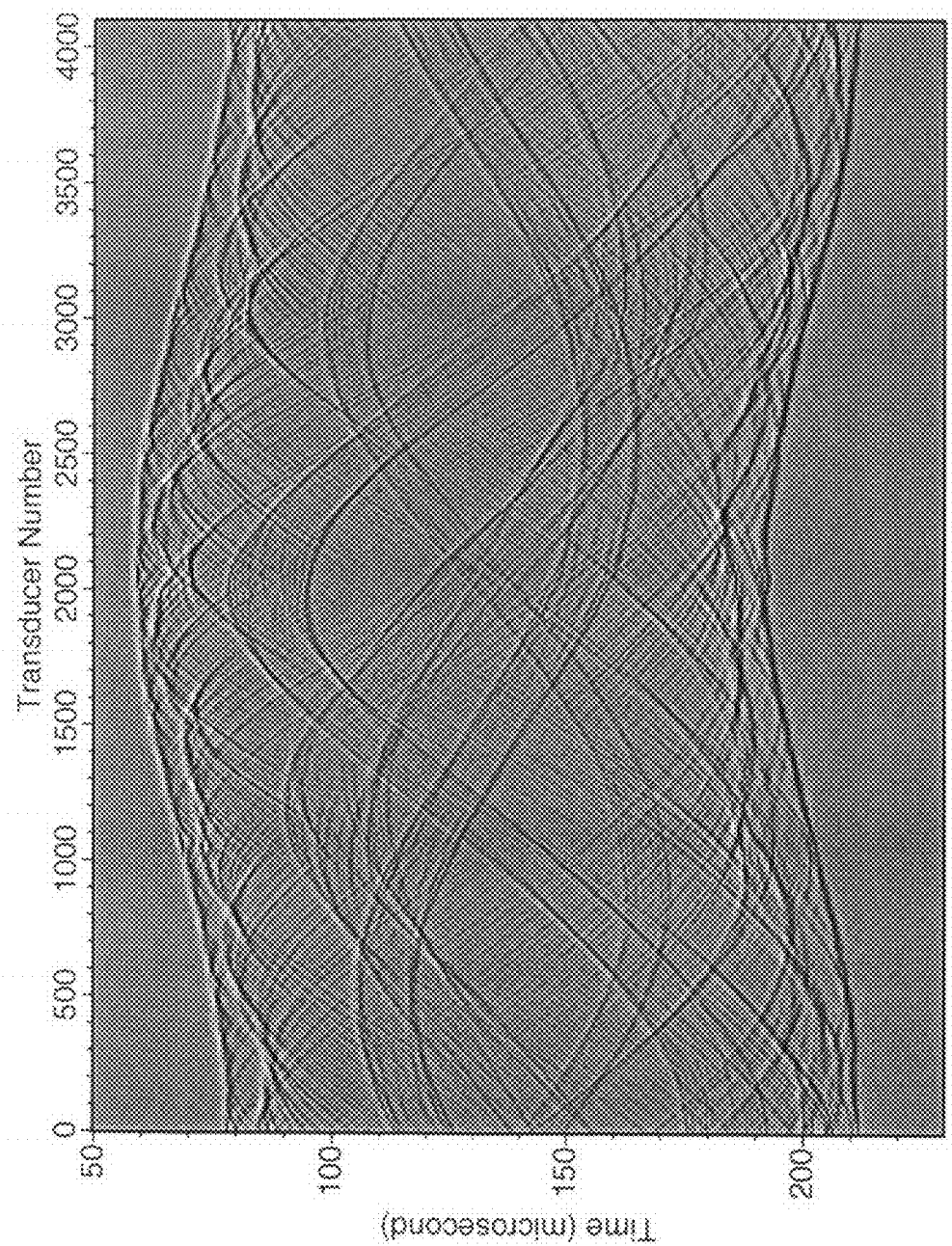
FIG. 11 is an image of computer-generated ultrasound pulse-echo data for the numerical breast phantom in FIG. 10A, according to aspects of the present invention.

FIG. 11 is computer-generated ultrasound pulse-echo data for the numerical breast phantom in FIG. 10A, and clearly shows scattering from the interfaces of the phantom tissues being imaged. The central frequency of the data is 1 Mhz. The synthetic pulse-echo data in the figure clearly shows ultrasonic scattering from the interfaces of four anomalies, in addition to other scattering signals.

Image reconstruction with the split-step Fourier propagator requires a heterogeneous sound-speed model. The heterogeneous sound-speed models of the numerical breast phantom are obtained using a time-of-flight transmission tomography method, [13] in which transmission ultrasound data are used instead of pulse-echo data. This tomography method is computationally efficient, particularly when only using a few iterations in tomography inversion to produce a reasonably accurate sound-speed image.

Figure 12B:
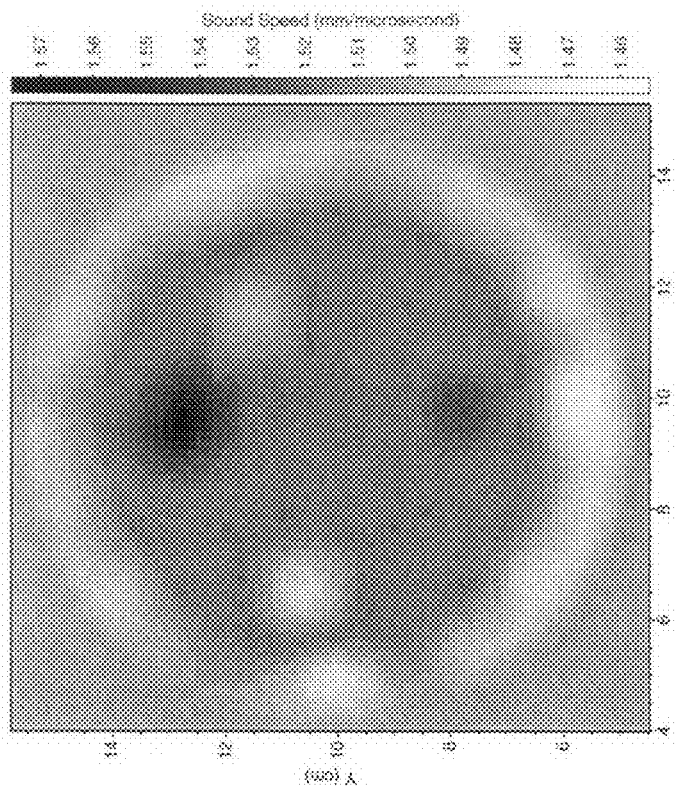
FIG. 12A-12B are images of sound-speed tomography results used for pulse-echo imaging based on two iterations and ten iterations, according to aspects of the present invention.
Figure 12A:
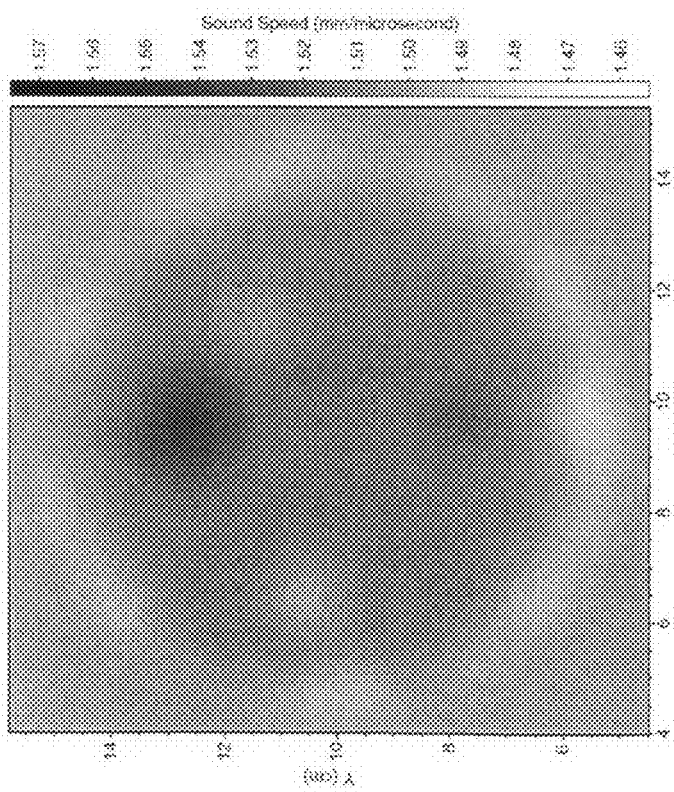

FIG. 12A-12B depict time-of-flight sound-speed tomography results used for pulse-echo imaging for the numerical phantom in FIG. 10A. In FIG. 12A time-of-flight tomography is shown in response to a preliminary scan of two iterations, while in FIG. 12B time-of-flight tomography is shown in response to ten iterations. It should be appreciated that FIG. 12B is more accurate being in response to additional iterations of the tomography inversion. It takes less than 20 seconds on a desktop computer to obtain the preliminary result as in FIG. 12A. Ultrasound pulse-echo imaging with the split-step Fourier propagator is conducted using the synthetic pulse-echo data in FIG. 11. In the image reconstructions, four different sound-speed models are used: a uniform one obtained using the average slowness of the numerical breast phantom in FIG. 10A, two time-of-flight sound-speed tomography results, as shown in FIGS. 12A and 12B, and the original (correct) sound-speed model of the phantom shown in FIG. 10A.

FIG. 13A-13D illustrates a comparison of reconstructed reflection images and compares ultrasound pulse-echo imaging using the split-step Fourier propagator with different sound-speed models. In FIG. 13A a phase-shift reconstruction is shown in response to a uniform sound-speed. In FIG. 13B-13D SSF reconstructions are utilized with heterogeneous sound-speed models from FIG. 12A, FIG. 12B, and FIG. 10A respectively. Image reconstructions with heterogeneous sound-speed models significantly improve image quality and resolution compared with that obtained using a uniform sound-speed as in FIG. 13A. As depicted in FIG. 13A, the phase-shift image reconstruction using a uniform sound-speed model produced a blurred image with significant artifacts. When even only using a preliminary tomography result (FIG. 12A) for SSF image reconstruction (FIG. 13B), the image resolution was significantly improved, and the image contained fewer artifacts than the phase-shift image reconstruction of FIG. 13A. As demonstrated in FIGS. 13B and 13C, imaging quality is further improved using the more accurate sound-speed tomography result shown in FIG. 12B, and is best when using the original sound-speed of the phantom in FIG. 10A for image reconstruction in FIG. 13D. FIG. 13D contains fewer image artifacts than FIGS. 13A-13C, but no exact sound-speed model will be available in practice. Nevertheless, the images in FIGS. 13A-13D are similar to the reflectivity depicted in FIG. 10B.

Figure 14B:
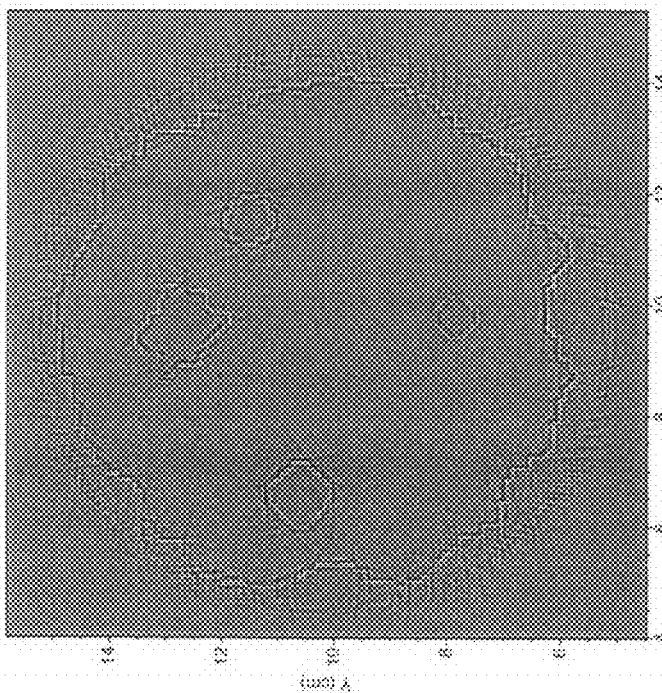
FIG. 14A-14B are images of differences detected between sound-speed tomography and the original phantom sound-speed tomograph, according to aspects of the present invention.
Figure 14A:
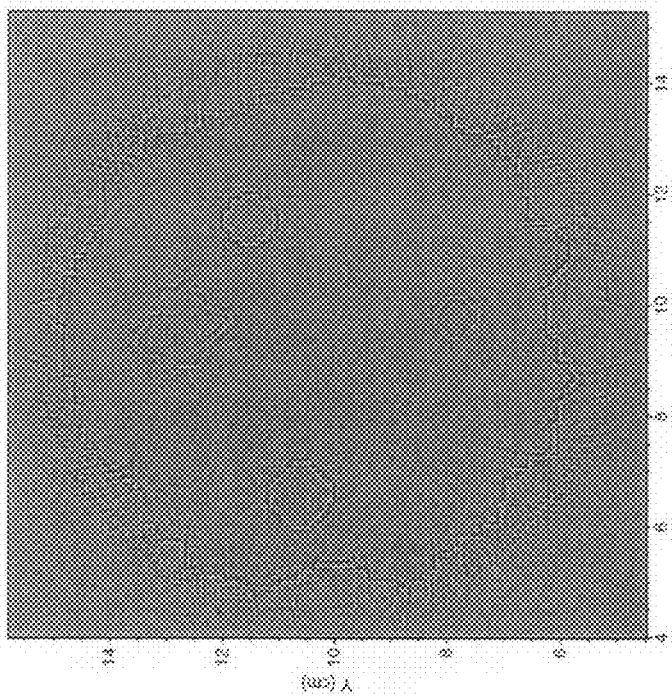

FIG. 14A-14B depict image differences between those obtained using sound-speed tomography and that which yielded the original (correct) phantom sound speed. These image differences are plotted using the same scale as that utilized in FIG. 13D. The images allow comparing differences more clearly, as FIG. 14A depicts the image differences between FIG. 13B and FIG. 13D, while FIG. 14B depicts the differences between FIG. 13C and FIG. 13D. It should be appreciated that the differences shown in FIG. 14B are smaller than those in FIG. 14A. It will be noted that the image differences decrease with increasing accuracy of sound-speed tomography results, or the image quality and resolution improve with increasing accuracy of the sound-speed models used for image reconstruction.

11. Imaging of Phantom Derived from In-Vivo Sound-Speed Tomography

Another numerical breast phantom which was utilized to test the capability of the split-step Fourier propagator for image reconstruction was derived from sound-speed tomography image of an in-vivo ultrasound breast dataset, collected using Karmanos Cancer Institute's ring transducer array. [9] The sound-speed image is obtained from the data using a time-of-flight transmission tomography method. [13] A numerical breast phantom is then derived from the sound-speed tomography image by removing the tomography artifacts.

FIG. 15A-15B illustrate a numerical breast phantom and reflectivity of the phantom, respectively. In FIG. 15A sound speed of a numerical breast phantom is shown derived from a sound-speed tomography result of in-vivo ultrasound breast data. The phantom contains heterogeneous breast tissues and a breast cancer with a higher sound speed than its surrounding tissues. The white solid circle in FIG. 15A is the ring array used to record synthetic pulse-echo data. In FIG. 15B the reflectivity within the phantom of FIG. 15A shows where changes of acoustic impedances occur. It will be appreciated that the low sound-speed regions in the phantom represent fatty tissues, and the high sound-speed region is a breast cancer. FIG. 15B depicts an enlarged display of reflectivity (normal reflection coefficient) within the phantom, showing the valuable standard ("gold standard") of reflection image reconstruction. The maximum value of the reflectivity is 0.0001639, which is two orders of magnitude smaller than that of the phantom in FIG. 10A.

A finite-difference time-domain acoustic-wave equation scheme is again used to compute ultrasound pulse-echo data for the numerical breast phantom in FIG. 15B. It is assumed that the densities of the phantom tissues are proportional to their sound speeds during finite-difference modeling.

Figure 16:
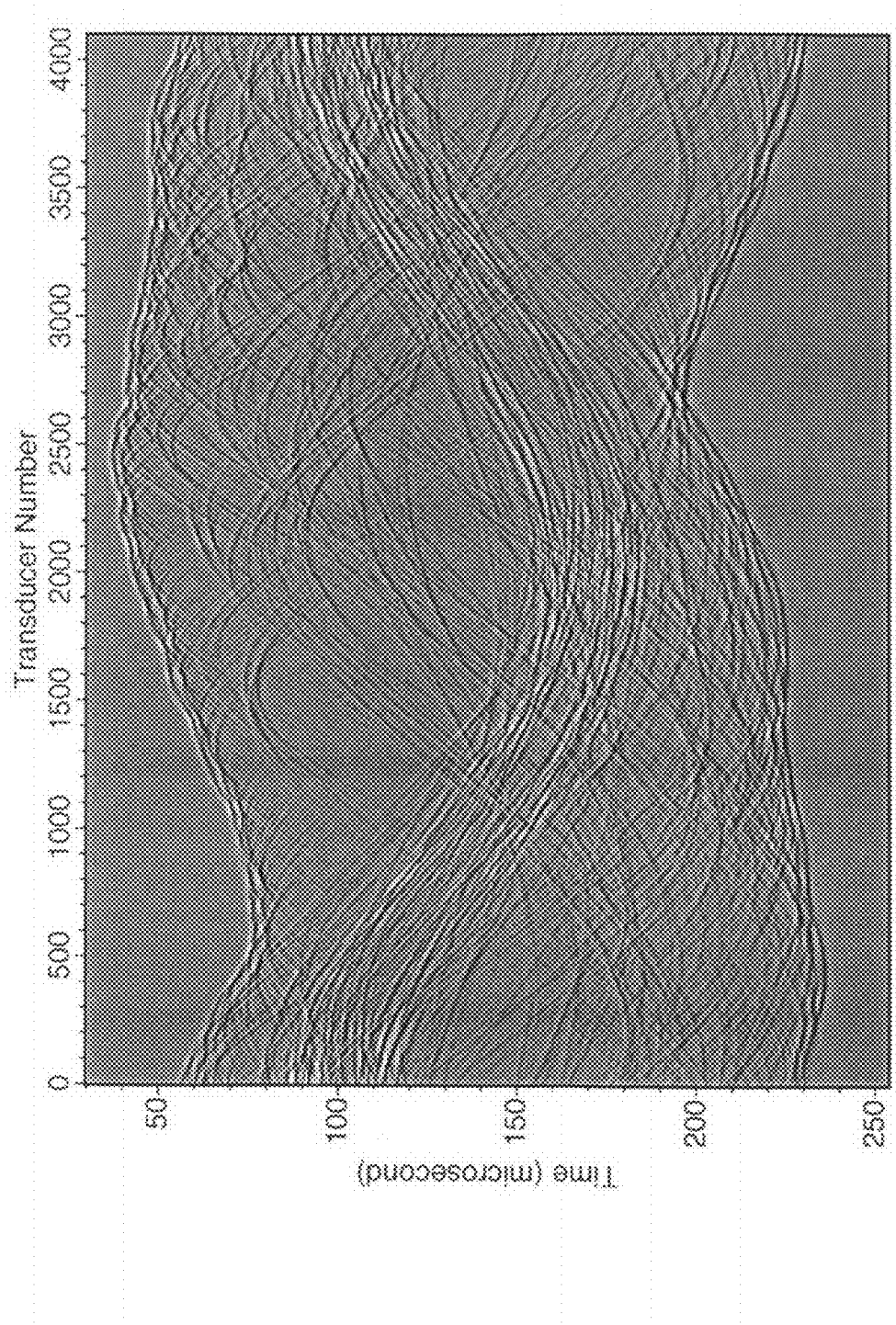
FIG. 16 is an image of computer-generated ultrasound pulse-echo data for the numerical breast phantom shown in FIG. 15A.

FIG. 16 is computer-generated ultrasound pulse-echo data for the numerical breast phantom in FIG. 15A. The central frequency of the data is 1 Mhz and the synthetic data recorded across multiple (e.g., 4096) transducers which are preferably equally distributed around the ring, for example within the white solid circle (approximate ring diameter of 20 cm) as shown in FIG. 15A. The data shows ultrasonic scattering from the heterogeneous phantom tissues.

Figure 17A:
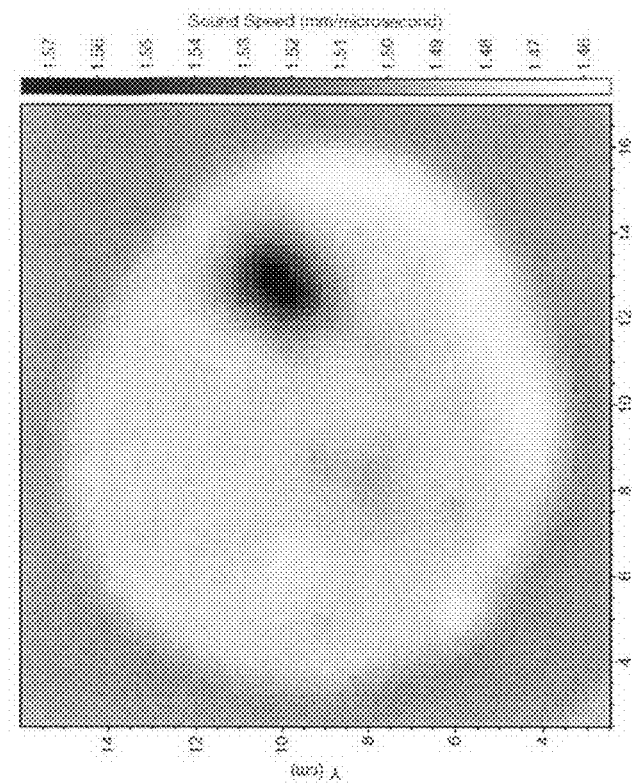
FIG. 17A-17B are images of tomography arising from different numbers of imaging iterations for the numerical breast phantom shown in FIG. 15A.
Figure 17B:
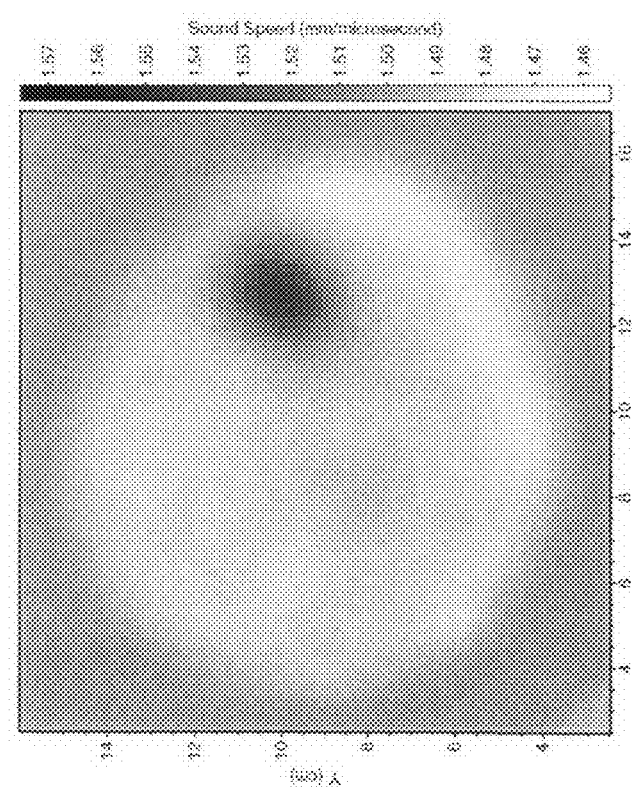

FIG. 17A-17B illustrate imaging results from two iterations and from ten iterations of the time-of-flight transmission tomography inversion for the numerical breast phantom in FIG. 15A. [13] FIG. 17B is a more accurate sound-speed model than FIG. 17A. These sound-speed models are utilized to reconstruct reflection images using the split-step Fourier propagator and the synthetic pulse-echo data in FIG. 16. For comparison, ultrasound pulse-echo imaging is also carried out using the phase-shift method with a uniform sound-speed model, and split-step Fourier image reconstruction with the correct phantom sound-speed.

Figure 18B:
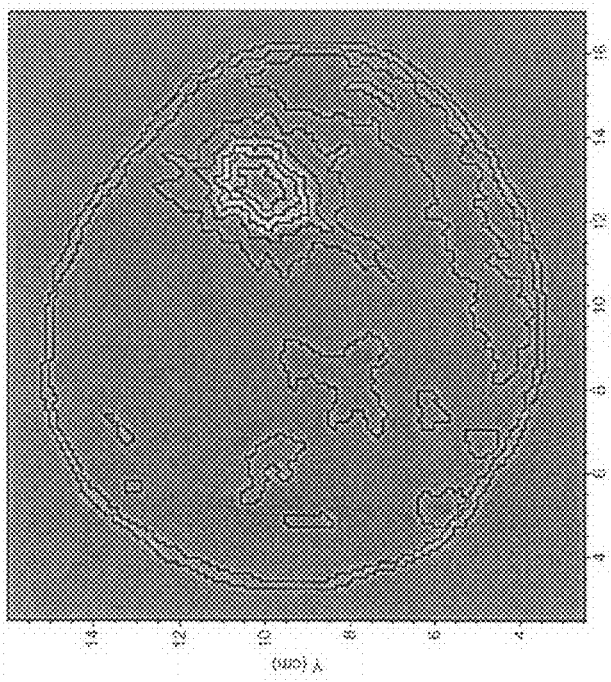
FIG. 18A-18D are images comparing reconstructed reflection images and ultrasound pulse-echo imaging using the split-step Fourier propagator, according to aspects of the present invention.
Figure 18A:
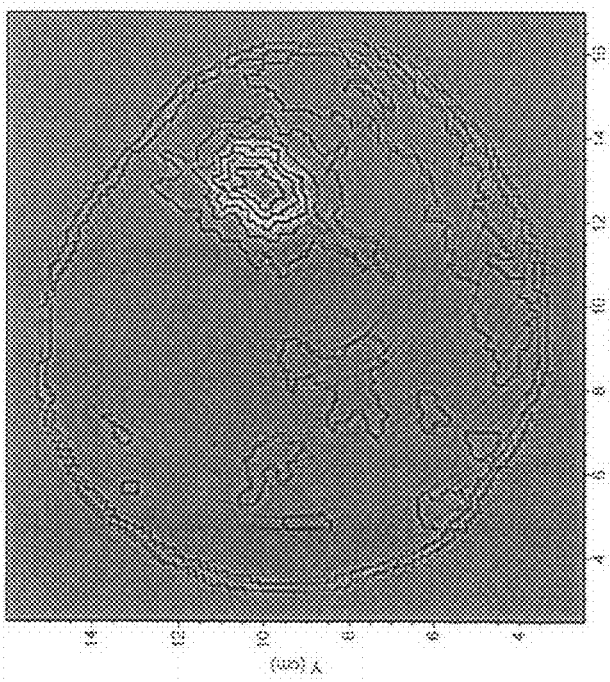
Figure 18D:
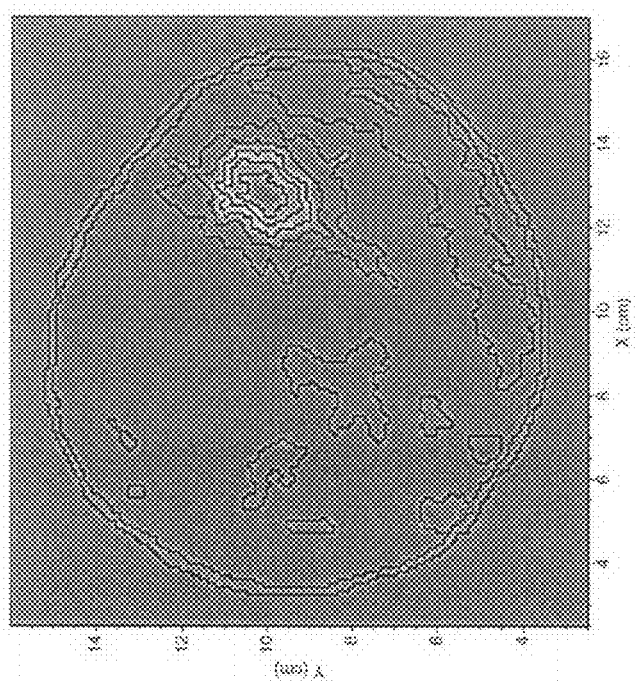
Figure 18C:
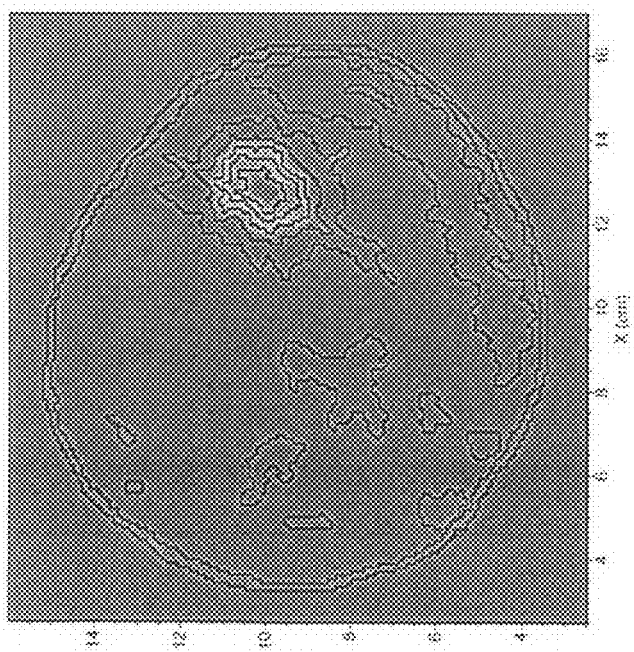

FIG. 18A-18D are similar to the image set of FIG. 13A-13D, albeit comparing different sound-speed images. In FIG. 18A is shown a phase-shift reconstruction with a uniform sound-speed. FIG. 18B-18D illustrate Split-Step Fourier (SSF) propagator reconstruction with a sound-speed model from FIG. 17A, FIG. 17B and FIG. 15A, respectively. It will be noted that the image reconstructions with heterogeneous sound-speed models (FIG. 18B-18D) provide significant improvements in image quality and resolution compared with that obtained using a uniform sound-speed as in FIG. 18A. The reconstructed images demonstrate once again that image quality and resolution are greatly enhanced by using reasonably accurate sound-speed models for image reconstruction. The images in FIG. 18B-18D closely match the reflectivity of the phantom as shown in FIG. 15B.

Figure 19A:
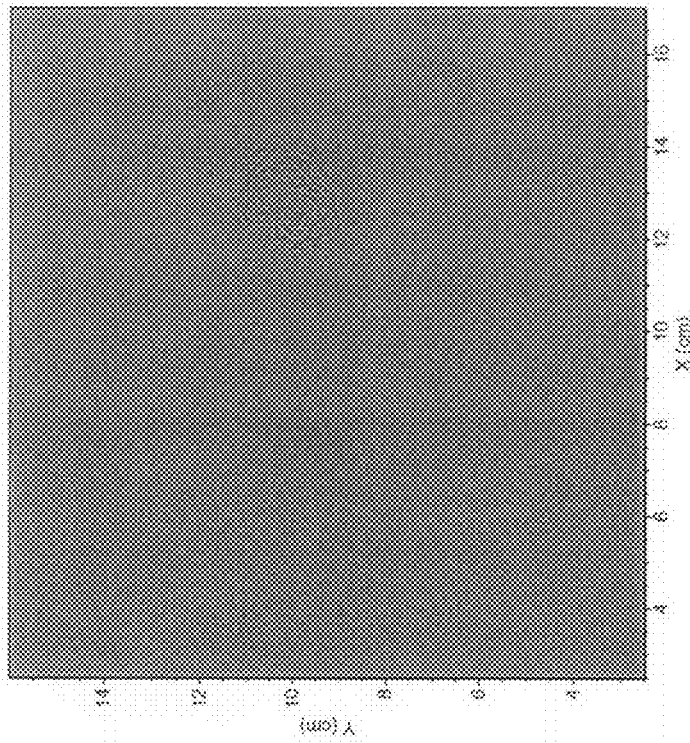
FIG. 19A-19B are images of differences between FIG. 18B and FIG. 18D, and between FIG. 18C and FIG. 18D.
Figure 19B:
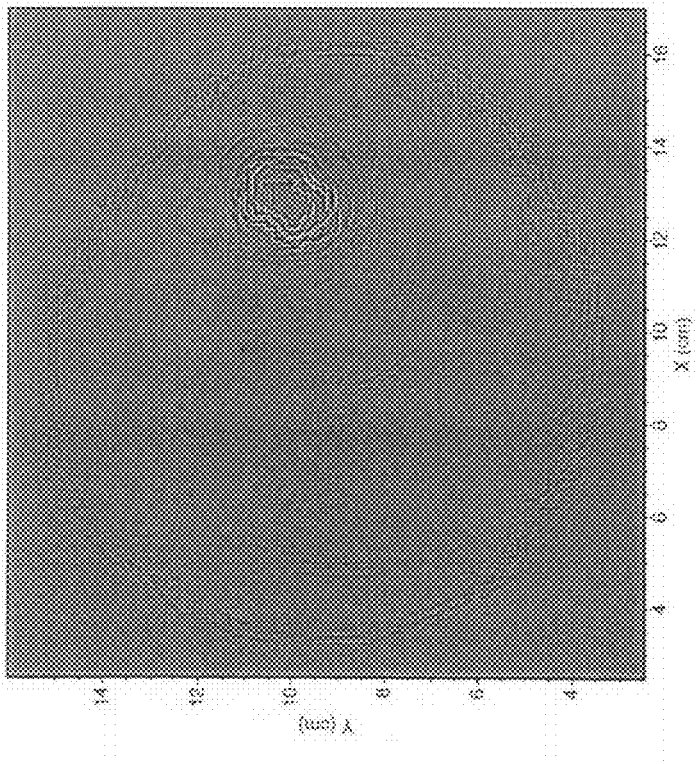

FIG. 19A-19B illustrate image differences between FIG. 18B and FIG. 18D, and between FIG. 18C and FIG. 18D, respectively. The image differences are clearly seen between those obtained using sound-speed tomography and that produced using the original (correct) phantom sound-speed. The differences in FIG. 19B are clearly smaller than those depicted in FIG. 19A. The image differences are plotted using the same scale as that in FIG. 18D. FIG. 19A-19B illustrate graphically that image differences decrease with increasing accuracy of sound-speed tomography results used for image reconstruction. Practically, image reconstruction using a sound-speed tomography result with five to ten iterations of the tomography inversion can produce high-quality and high-resolution reflection images.

12. Verification of Sampling Criterion of Ring Array Wavefields

The sampling criterion of wavefields needed to image objects within a ring array has recently been developed [21] and is given by:

$$\Delta < \frac{\lambda R}{2r_0} \qquad (6)$$

where $\Delta$ is the transducer spatial interval, $\lambda$ is the wavelength, R is the radius of the ring array, and $r_0$ is radius of the object to be imaged.

In the image reconstruction studies undertaken using the numerical breast phantom in FIG. 15A and the pulse-echo data in FIG. 16, $\lambda=1.5$ mm, R=100 mm, $r_0 \approx 60$ mm. Therefore, the transducer interval must satisfy $\Delta < 1.25$ mm according to Eq. (6).

Figure 20A:
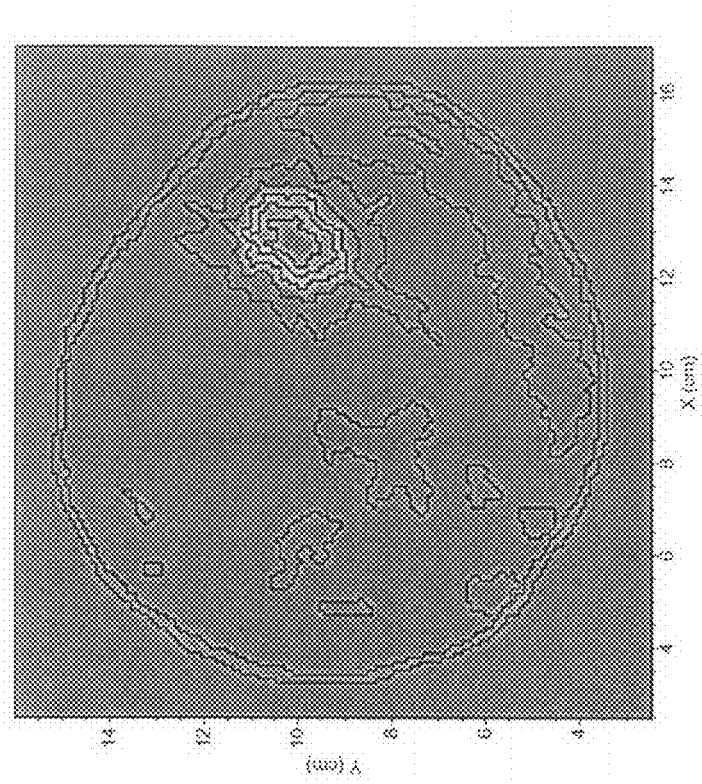
FIG. 20A-20D are images of ultrasound pulse-echoing for the numerical breast phantom in FIG. 15A, shown in response to different numbers of transducers in the ring array.
Figure 20B:
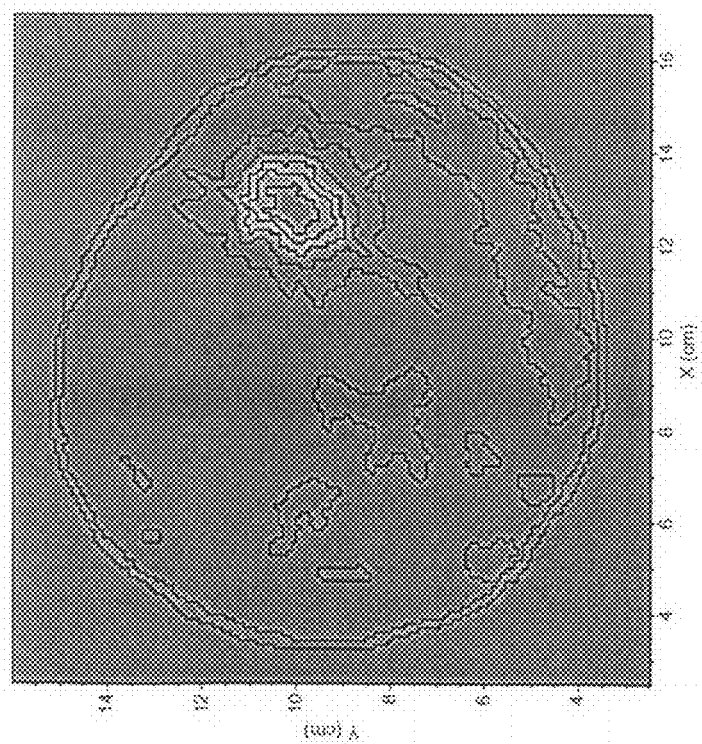
Figure 20D:
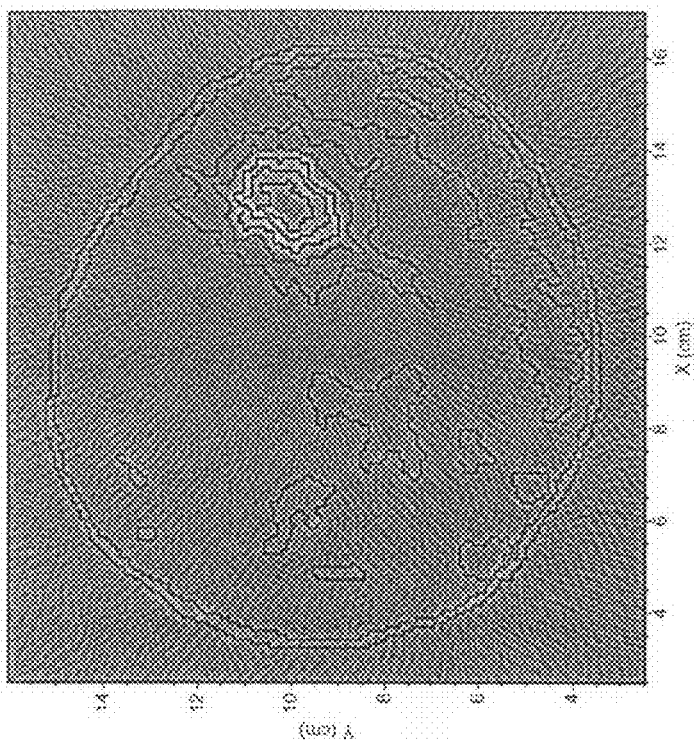
Figure 20C:
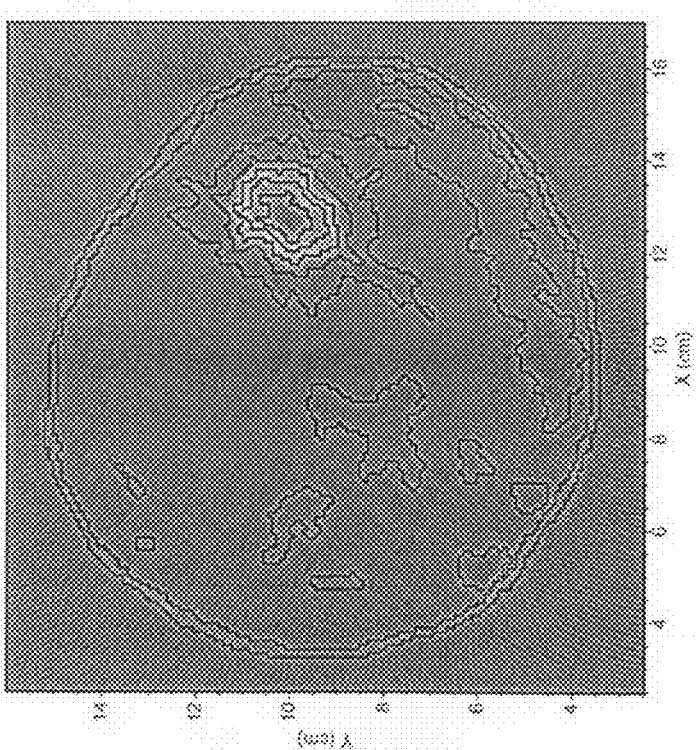

FIG. 20A-20D is ultrasound pulse-echo imaging results for the numerical breast phantom in FIG. 15A with a different number of transducers in the ring array, specifically FIG. 20A is 2048; FIG. 20B is 1024; FIG. 20C is 512; and FIG. 20D is 256. The sound speed used for image reconstruction is that shown in FIG. 17B. It should be appreciated that imaging quality decreases significantly when the number of transducers is less than 512, or when the transducer spacing violates the sampling criterion for the ring array. These split-step Fourier image reconstructions were performed recording ultrasound pulse-echo data as shown in FIG. 16. The corresponding transducer intervals are as follows: FIG. 20A is 0.31 mm; FIG. 20B is 0.61 mm; FIG. 20C is 1.23 mm; and FIG. 20D is 2.45 mm. The sound-speed tomography model depicted in FIG. 17B is used for the image reconstruction. The transducer intervals for FIGS. 20A-20C satisfy the sampling criterion of wavefields for the ring array, but the sparse arrangement of the transducer of FIG. 20D does not, wherein its use can lead to significant image artifacts inside and outside the phantom area. Even though FIG. 20C contains some image artifacts outside the phantom region, the image within the phantom has significantly fewer artifacts than that in FIG. 20D.

13. Section C: Conclusions

An inventive ultrasound pulse-echo imaging method using a split-step Fourier propagator has been taught herein. The method uses heterogeneous sound-speed models obtained from time-of-flight transmission tomography for image reconstruction to approximately compensate for ultrasonic scattering effects. The discussion investigated the capability of this method for reflection image reconstruction using two different numerical breast phantoms and synthetic pulse-echo data recorded by a ring array. It has been demonstrated herein that image reconstruction with the split-step Fourier propagator and a heterogeneous sound-speed model significantly improve image resolution and quality, even when using only a preliminary estimate of the sound speed. The spatial sampling criterion of wavefields for a ring array has also been numerically verified. Waveform tomography has the potential to produce higher-resolution sound-speed images than time-of-flight transmission tomography. [22] It will be appreciated that additional study into sound-speed models obtained using waveform tomography for ultrasound reflection image reconstruction can lead to further improvements in image quality and resolution. In addition, further study into the capability of the ultrasound reflection image reconstruction with the split-step Fourier propagator could lead to more realistic and complex numerical renditions of breast phantoms, and medical application of the in-vivo ultrasound breast data collected using a ring array.

14. Section C: References

[1] S. Hughes, "Medical ultrasound imaging," *Physics Education*, pp. 468-475, 2001.

[2] S. J. Norton and M. Linzer, "Ultrasonic reflectivity tomography: reconstruction with circular transducer arrays," *Ultrasonic Imaging* 2, pp. 154-184, 1979.

[3] J. S. Schreiman, J. J. Gisvold, J. F. Greenleaf, and R. C. Bahn, "Ultrasound transmission computed tomography of the breast," *Radiology* 150, pp. 523-530, 1984.

[4] P. J. Littrup, N. Duric, S. Azevedo, D. H. Chambers, J. V. Candy, S. Johnson, G. Auner, J. Rather, and E. T. Holsapple, "Computerized Ultradound Risk Evaluation (CURE) system: Development of combined transmission and reflection ultrasound with new reconstruction algorithms for breast imaging," *Acoustical Imaging* 26, pp. 175-182, 2002.

[5] R. Stotzka, G. Gobel, and K. Schlote-Holubek, "Development of transducer arrays for ultrasoundcomputertomography," in *Ultrasonic Imaging and Signal Processing*, W. F. Walker and M. Insana, eds., *Proc. SPIE Medical Imaging* 5035, pp. 513-520, 2003.

[6] N. Duric, P. J. Littrup, O. Rama, and E. T. Holsapple, "Computerized ultrasound risk evaluation (CURE): First clinical results," *Acoustical Imaging* 28, 2005.

[7] S. A. Johnson, D. T. Borup, J. W. Wiskin, m Berggren, B. H. anf F Setinsek, S. Olsen, and K. Callahan, "From laboratory to clinical trials: An odyssey of ultrasound inverse scattering imaging for breast cancer diagnosis," *J. Acoust. Soc. Am.* 120, p. 3023, 2006.

[8] R. C. Waag and R. J. Fedewa, "A ring transducer system for medical ultrasound research," *IEEE Transactions on Ultrasonics, Ferroelectrice, and Frequency Control* 53, pp. 1707-1718, 2006.

[9] N. Duric, P. Littrup, L. Poulo, A. Babkin, R. Pevzner, E. Holsapple, and O. Rama, "Detection of breast cancer with ultrasound tomography: First results with the computerized ultrasound risk evaluation (c.u.r.e) prototype," *Medical Physics* 32, 2007 (accepted).

[10] M. P. Andre, H. S. Janee, P. J. Martin, G. P. Otto, B. A. Spivey, and D. A. Palmer, "High-speed data acquisition in a diffraction tomography system employing large-scale toroidal arrays," *International Journal of Imaging Systems and Technology* 8, pp. 137-147, 1997.

[11] D. H. Chambers and P. Littrup, "Ultrasound imaging using diffraction tomography in a cylindrical geometry," in *Ultrasonic Imaging and Signal Processing*, M. Insana and W. F. Walker, eds., *Proc. SPIE Medical Imaging* 4687, pp. 412-420, 2002.

[12] N. Duric, P. Littrup, E. T. Holsapple, A. Babkin, R. Duncan, A. Kalinin, R. Pevzner, and M. Tokarev, "Ultrasound tomography of breast tissue," in *Ultrasonic Imaging and Signal Processing*, W. F. Walker and M. Insana, eds., *Proc. SPIE Medical Imaging* 5035, 2003.

[13] Y. Quan and L. Huang, "Sound-speed tomography using first-arrival transmission ultrasound for a ring array," in *Ultrasonic Imaging and Signal Processing*, S. Y. Emelianov and S. A. McAleavey, eds., *Proc. SPIE Medical Imaging* 6513, 2007.

[14] R. H. Hardin and F. D. Tappert, "Applications of the split-step Fourier method to the numerical solution of the nonlinear and variable coefficient wave equations," *SIAM Rev.* 15, p. 423, 1973.

[15] F. D. Tappert, "The parabolic approcimation method," in *Wave Propagation in Underwater Acoustics*, J. B. Keller and J. S. Papadakis, eds., pp. 224-287, 1977.

[16] P. L. Stoffa, J. T. Fokkema, R. M. de Luna Freire, and W. P. Kessinger, "Split-step Fourier migration," *Geophysics* 55, pp. 410-421, 1990.

[17] L. Huang and M. C. Fehler, "Accuracy analysis of the split-step Fourier propagator: implications for seismic modeling and migration," *Bull. Seis. Soc. Am.* 88, pp. 18-29, 1998.

[18] F. B. Jensen, W. A. Kuperman, M. B. Porter, and H. Schmidt, *Computational Ocean Acoustics*, Springer-Verlag, New York, 2000.

[19] L. Huang, N. Duric, and P. Littrup, "Breast imaging with time-reversed ultrasound," in *Ultrasonic Imaging and Signal Processing*, S. Emelianov and W. F. Walker, eds., *Proc. SPIE Medical Imaging* 6147, pp. 156-167, 2006.

[20] L. Huang, N. Duric, and P. Littrup, "Ultrasonic breast imaging using a wave-equation migration method," in *Ultrasonic Imaging and Signal Processing*, W. F. Walker and M. Insana, eds., *Proc. SPIE Medical Imaging* 5035, pp. 432-439, 2003.

[21] F. Simonetti, L. Huang, and N. Duric, "On the spatial sampling of wave fields with circular ring apertures," *Journal of Applied Physics*, 2007 (accepted).

[22] R. G. Pratt, L. Huang, N. Duric, and P. Littrup, "Sound-speed and attenuation of the breast tissue using waveform tomography of transmission ultrasound data," in *Physics of Medical Imaging*, J. Hsieh and M. J. Flynn, eds., *Proc. SPIE Medical Imaging* 6510, 2007.

Section D

It should be appreciated that although the methods described were directed at ultrasonic breast imaging, these techniques can be implemented within any number of ultrasonic tissue imaging apparatus. The method is particularly well-suited for implementation on a system which receives reflective ultrasonic waveform information (waveform tomography) and utilizes a computer for processing to perform the reconstruction of those signals. It should be appreciated, however, that the aspects of the invention can be implemented on any desired combination of software and hardware as will be recognized by one of ordinary skill in the art.

Figure 21:
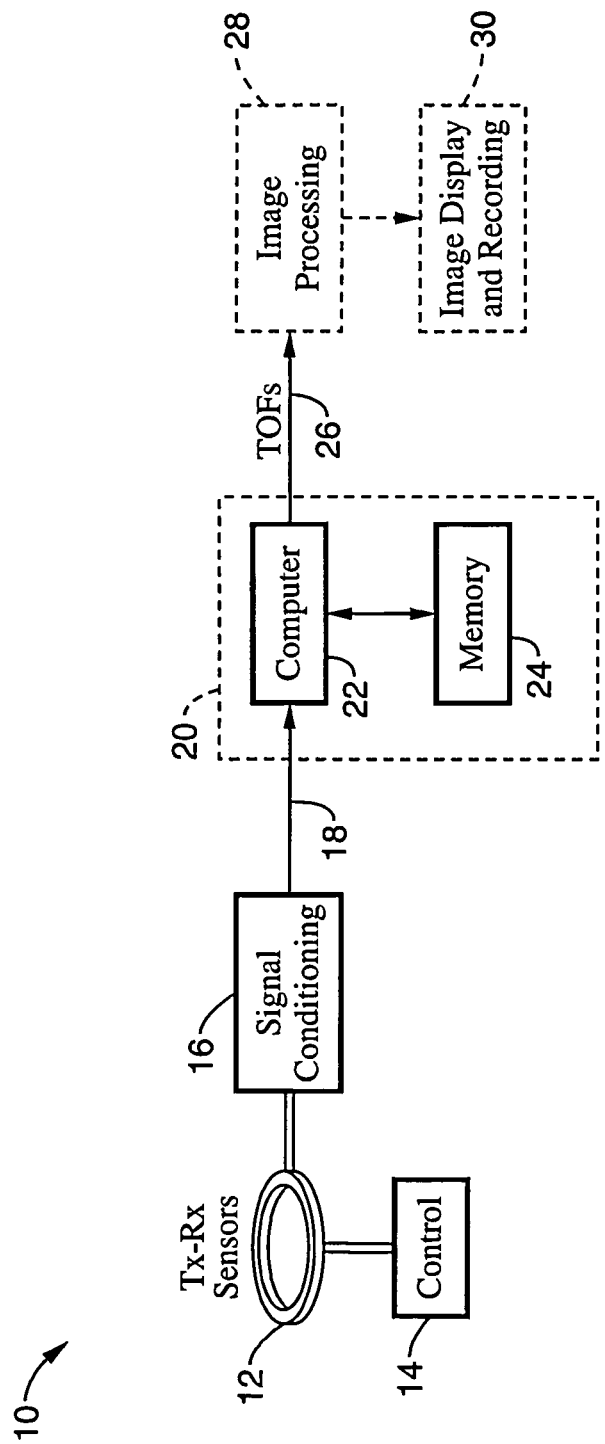
FIG. 21 is a block diagram of an apparatus for performing the reflection imaging according to aspects of the present invention.

FIG. 21 illustrates an embodiment 10 of an ultrasonic imaging apparatus according to the present invention. A sensor head 12 is shown exemplified as a ring configured for ultrasonic imaging (e.g., breast tissue imaging), although it can be configured in any desired configuration for various forms of tissue testing. The sensor head 12 is configured with transmitters and receivers controlled by block 14. All necessary data from the sensor head is conditioned as necessary in signal conditioning block 16, from which data 18 on a plurality of ultrasonic signals is communicated to a computing device 20 containing at least one processing element 22 and memory 24. The ultrasonic signals received by the computer contain more than time-of-flight information, and preferably contain the entire waveforms to provide accurate recontruction. Programming executable on computer 22 is configured for retention in memory 24, and for executing the described method steps according to the present invention, including those recited for the split-step Fourier transform propagator.

The reconstructed image output can be utilized internal to the computer or be output 26 from the computer for use by image processing equipment 28 and image display and/or storage elements 30. It will thus be appreciated that numerous medical ultrasonic devices can be configured according to the teachings of the present invention to improve resolution and quality of the ultrasonic information.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method of ultrasound reflective image reconstruction for waveforms generated within a medical ultrasound imaging device, comprising:
   (a) receiving a heterogeneous sound-speed model of a tissue region being imaged;
   (b) receiving ultrasonic waveform information in response to reflection data for the tissue region being imaged; and
   (c) reconstructing a reflection image using a split-step Fourier transform propagator configured for recursive inward continuation of ultrasonic wavefields in the frequency-space and frequency-wave number domains by:
      (i) applying a first phase-shift term to said ultrasonic waveform information in the frequency-wave number domain for propagation in a reference medium; and
      (ii) applying a second phase-shift term to said ultrasonic waveform information in the frequency-space domain to compensate for ultrasonic scattering effects of heterogeneities within said tissue region.

2. A method as recited in claim 1, further comprising computing a sound-speed contrast as the reciprocal of the refraction index for the ultrasonic waveform information.

3. A method as recited in claim 1, wherein in response to a detailed sound-speed approximation with optimized free coefficients, the method provides a globally optimized Fourier finite-difference image reconstruction.

4. A method as recited in claim 3, wherein said optimized free coefficients are generated in response to minimizing the phase-error for the entire sound-speed perturbation range of the tissue region to obtain optimized free coefficients.

5. A method as recited in claim 1:
   wherein said method is based on waveform tomography instead of time-of-flight tomography; and
   wherein said waveform tomography is performed in response to Fourier transforms to reduce dispersion.

6. A method as recited in claim 1, wherein said method properly accounts for ultrasound scattering from tissue region heterogeneities.

7. A method as recited in claim 1, wherein said ultrasonic waveform information comprises information about the entire waveform, and is not limited to time-of-flight (TOF) information.

8. A method as recited in claim 1, wherein said propagator is optimized for the sound-speed perturbation range within the tissue being imaged.

9. A method as recited in claim 1, wherein said propagator is configured for resolving two one-way wave equations describing wave propagation in opposite directions.

10. A method of ultrasound reflective image reconstruction for waveforms generated within a medical ultrasound imaging device, comprising:
    (a) receiving a heterogeneous sound-speed model of a tissue region being imaged;
    (b) receiving ultrasonic waveform information in response to reflection data for the tissue region being imaged; and
    (c) reconstructing a reflection image from the ultrasonic waveform information using a split-step Fourier transform propagator configured for recursive inward continuation of ultrasonic wavefields in the frequency-space and frequency-wave number domains by:
       (i) Fourier transforming of acoustic wavefield $U(x, z; \omega)$ with respect to x;
       (ii) applying a phase-shift term $e^{-ik_z \Delta z}$ to the wavefield in the frequency-wave number $(\omega - k_x)$ domain, where $k_z = \sqrt{k_0^2 - k_x^2}$ with $k_0 = \omega/v_0$, and $k_x$ is the wave number along the x-coordinate;
       (iii) inverse Fourier transformation of the resulting wavefield into the frequency-space $(\omega - x)$ domain; and
       (iv) applying a phase-shift term $e^{-i\omega(s-s_0)}$ to compensate for ultrasonic scattering effects of heterogeneities to generate the extrapolated acoustic wavefield.

11. A method as recited in claim 10, further comprising computing a sound-speed contrast as the reciprocal of the refraction index for the ultrasonic waveform information.

12. A method as recited in claim 10, wherein in response to a detailed sound-speed approximation with optimized free coefficients, the method provides a globally optimized Fourier finite-difference image reconstruction.

13. A method as recited in claim 12, wherein said optimized free coefficients are generated in response to minimizing the phase-error for the entire sound-speed perturbation range of the tissue region to obtain optimized free coefficients.

14. A method as recited in claim 10:
    wherein said method is based on waveform tomography instead of time-of-flight tomography; and
    wherein said waveform tomography is performed in response to Fourier transforms to reduce dispersion.

15. A method as recited in claim 10, wherein said method properly accounts for ultrasound scattering from tissue region heterogeneities.

16. A method as recited in claim 10, wherein said ultrasonic waveform information comprises information about the entire waveform, and is not limited to time-of-flight (TOF) information.

17. A method as recited in claim 10, wherein said propagator is optimized for the sound-speed perturbation range within the tissue being imaged.

18. A method as recited in claim 10, wherein said propagator is configured for resolving two one-way wave equations describing wave propagation in opposite directions.

19. An apparatus for reconstructing reflective ultrasound images for waveforms generated within a medical ultrasound imaging device, comprising:
   (a) means for receiving a plurality of ultrasound waveforms from an ultrasound transmitter-receiver device directed for reflection from a tissue region being imaged;
   (b) a computer processor and memory coupled to said means; and
   (c) programming executable on said processor for:
      (i) receiving a heterogeneous sound-speed model of the tissue region from tomography;
      (ii) receiving ultrasonic waveform information in response to reflection data for the tissue region being imaged; and
      (iii) reconstructing a reflection image using a split-step Fourier transform propagator configured for recursive inward continuation of ultrasonic wavefields in the frequency-space and frequency-wave number domains by:
         (1) applying a first phase-shift term to said ultrasonic waveform information in the frequency-wave number domain for propagation in a reference medium; and
         (2) applying a second phase-shift term to said ultrasonic waveform information in the frequency-space domain to compensate for ultrasonic scattering effects of heterogeneities within said tissue region.

20. A computer-readable media executable on a computer apparatus configured for reconstructing reflective ultrasound images for waveforms generated within a medical ultrasound imaging device, comprising:
   (a) a computer readable, non-transitory, media containing programming executable on a computer processor configured for processing ultrasound waveforms in response to receiving a plurality of entire ultrasound waveforms from an ultrasound transducer device directed for reflection from a tissue region being imaged; and
   (b) wherein said programming is configured for:
      (i) receiving a heterogeneous sound-speed model of the tissue region from tomography;
      (ii) receiving ultrasonic waveform information in response to reflection data for the tissue region being imaged; and
      (iii) reconstructing a reflection image using a split-step Fourier transform propagator configured for recursive inward continuation of ultrasonic wavefields in the frequency-space and frequency-wave number domains by:
         (1) applying a first phase-shift term to said ultrasonic waveform information in the frequency-wave number domain for propagation in a reference medium; and
         (2) applying a second phase-shift term to said ultrasonic waveform information in the frequency-space domain to compensate for ultrasonic scattering effects of heterogeneities within said tissue region.

* * * * *